(12) United States Patent
Allen et al.

(10) Patent No.: US 6,624,343 B1
(45) Date of Patent: Sep. 23, 2003

(54) HEXOSE CARRIER PROTEINS

(75) Inventors: Stephen M Allen, Wilmington, DE (US); J. Antoni Rafalski, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 09/679,686

(22) Filed: Oct. 5, 2000

Related U.S. Application Data

(63) Continuation of application No. PCT/US99/07561, filed on Apr. 7, 1999
(60) Provisional application No. 60/081,131, filed on Apr. 9, 1998.

(51) Int. Cl.[7] .......................... A01H 1/00; C07H 21/04; C12N 5/14
(52) U.S. Cl. .......................... 800/278; 435/6; 435/69.1; 435/410; 435/419; 435/252.3; 435/320.1; 530/350; 530/370; 536/23.1; 536/23.6; 536/24.1; 800/284; 800/295
(58) Field of Search .......................... 435/6, 69.1, 410, 435/419, 252.3, 320.1; 530/350, 370; 536/23.1, 23.6, 24.1; 800/278, 284, 295

(56) References Cited

U.S. PATENT DOCUMENTS 5,658,773 A * 8/1997 Bennett et al.

OTHER PUBLICATIONS

Alfons Weig et al., J. Plant Physiol., vol. 143:178–183, 1994, Isolation of a Family of cDNA Clones from *Ricinus communis* L. with Close Homology to the Hexose Carriers.
Maria J. Harrison, The Plant Journal, vol. 9(4):491–503, 1996, A Sugar Transporter from Medicago truncatula: altered expression pattern in roots during vesicular–arbuscular (VA) mycorrhizal associations.
National Center for Biotechnology Information General Identifier No. 99758, Sauer, N. et al., Feb. 10, 1995.
National Center for Biotechnology Information General Identifier No. 1353516, Harrison, M.J., A sugar transporter from Medicago truncatula: altered expression pattern in roots during vesicular–arbuscular (VA) mycorrhizal associations, Oct. 1, 1996.
National Center for Biotechnology Information General Identifier No. 1708191, Weig, A. et al., Oct. 1, 1996.
National Center for Biotechnology Information General Identifier No. 347853, Bugos, R.C. et al., Glucose transporter cDNAs from sugarcane, Apr. 2, 1999.
National Center for Biotechnology Information General Identifier No. 3540199, Federspiel, N.A. et al., Jan. 11, 1999.
National Center for Biotechnology Information General Identifier No. 4138724, Delrot, S., Jan. 7, 1999.
Robert C. Bugos et al., Plant Physiol., vol. 103:1469–1470, 1993, Glucose Transporter cDNAs from Sugarcane.
Database EMBL Accession No. 024245, Jan. 1, 1998, Nehls U. et al., Sugar transport protein from *Picea excelsa*, XP002109845.
Database EMBL Accession No. Q39228, Nov. 1, 1996, Truernit E. et al., Sugar transport protein STP4 from *Arabiodopsis thaliana*, XP002109846.
Database EMBL Accession No. L21753, Jan. 7, 1994, Bugos, R.C. et al., Saccharum sp. glucose transporter mRNA, XP002109847.
National Center for Biotechnology Information General Identifier No. 1353516, Harrison, M.J., A sugar transporter from *Medicago truncatula*: altered epxression pattern in roots during vesicular–arbuscular (VA) mycorrhizal associations, Aug. 26, 1996, XP002109848.
Database EMBL Accession No. X55350, May 22, 1991, Sauer, N., A Thaliana STP1 mRNA for glucose transporter, XP002109489.
National Center for Biotechnology Information General Identifier No. 467319, Oct. 24, 1995, Weig, A. et al., Functional identification of a hexose carrier (HEX6) from *Ricinus communis* L, XP002109850.
National Center for Biotechnology Information General Identifier No. 1708191, Weig, A. et al., Oct. 1, 1996, XP002109851.
National Center for Biotechnology Information General Identifier No. 99758, Feb. 10, 1995, Sauer, N. et al., XP002109852.

* cited by examiner

Primary Examiner—Phuong T. Bui

(57) ABSTRACT

This invention relates to an isolated nucleic acid fragment encoding a hexose carrier protein. The invention also relates to the construction of a chimeric gene encoding all or a portion of the hexose carrier protein, in sense or antisense orientation, wherein expression of the chimeric gene results in production of altered levels of the hexose carrier protein in a transformed host cell.

10 Claims, 5 Drawing Sheets

```
                                                           60
SEQ ID NO:19 (gi 17081291)  MAAGLAITSEG-GQ-----YNGRMTSFVALSCMMAAMGGVIFGYDIGVSGGVTSMDPFLKK
SEQ ID NO:20 (gi 347853)    ------------------------------------------------------------
SEQ ID NO:21 (gi 3540199)   MAGGALTDEGGLK-RAHLYEHRITSYFIFACIVGSMGGSLFGYDLGVSGGVTSMDDFLKE-
SEQ ID NO:22 (gi 99758)     MAG-GFVSQTP-GVRN--YNYKLTPKVFVTCFIGAFGGLIFGYDLGISGGVTSMEPFLEE-
SEQ ID NO:23 (gi 1353516)   MAGGI-PIGG-GNKE--YPGNLTPFVTITCIVAAMGGLIFGYDIGISGGVTSMDPFLKK--
SEQ ID NO:24 (gi 4138724)   MPAVGGFDKGT-G-KA--YPGNLTPYVTVCVVAAMGGLIFGYDIGISGGVTSMAPFLQK--
SEQ ID NO:2                 MAGGFGGGGAA-AGRAELYEGKITGYFILACIVGSFGGSLFGYDLGVSSGVTSMDDFLVK-
SEQ ID NO:4                 MAG-GGIVNTG-GGKD--YPGKLTLFVLLTCIVAATGGLIFGYDIGISGGVTSMNPFLEK-
SEQ ID NO:6                 ------------------------------------------------------------
SEQ ID NO:8                 ------------------------------------------------------------
SEQ ID NO:10                MAG-GAVVSTG-AGKD--YPGKLTLFVFFTCVVAATGGLIFGYDIGISGGVTSMDPFLRK-
SEQ ID NO:12                MAGGGVAALGVKKERAAEYKGRMTLAVGMACLVAAVGGAIFGYDIGISGGVTSMDFLKK--
SEQ ID NO:14                MPAVGG-ISNG-GGKE--YPGSLTPFVTVTCIVAAMGGLIFGYDIGISGGVTSMDPFLLK-
SEQ ID NO:16                ------------------------------------------------------------
SEQ ID NO:18                MAG-GAVVNTS-GGKD--YPGRLTLFVFFTCVVAATGGLIFGYDIGISGGVTSMNPFLKK-

120
SEQ ID NO:19 (gi 17081291)  FFPDVYRKMKEDTEISNYCKFDSQLLTSFTSSLYVAGLVASFFASSVTRAFGRKPSILLG
SEQ ID NO:20 (gi 347853)    ------------------------------------------------------------
SEQ ID NO:21 (gi 3540199)   FFPGIYKRKQMHLNETDYCKFDSQLLTLFTSSLYFAGLISTFGASYVTRIYGRRGSILVG
SEQ ID NO:22 (gi 99758)     FFPYVYKKMKSA-HENEYCRFDSQLLTLFTSSLYVAALVSSLFASTITRVFGRKWSMFLG
SEQ ID NO:23 (gi 1353516)   FFPAVYRKKNKDKSTNQYCQYDSQTLMFTSSLYLAALLSSLVASTITRRFGRKLSMLFG
SEQ ID NO:24 (gi 4138724)   FFPSVYRKEALDKSTNQYCKFDSETLLFTSSLYLAALLSSLVAATVTRKFGRKLSMLFG
SEQ ID NO:2                 FFPDVYRRKQAHLHETDYCKYDNQVLTLFTSSLYFAGLVSTFGASYVTKRHGRRASIMGG
SEQ ID NO:4                 FFPEVYRKKQ-EAKTNQYCKYDNQLLQTFTSSLYLAALVASFFAATVTRAVGRKWSMLVG
SEQ ID NO:6                 ------------------------------------------------------------
SEQ ID NO:8                 ------------------------------------------------------------
SEQ ID NO:10                FFPEVYRKKQMADKNNQYCKYDNQLLQTFTSSLYLAALVSSFFAATVTRVLGRKWSMFAG
SEQ ID NO:12                FFPEVVFRKKNDD-GQNNYCKYDNQGLSAFTSSLYLAGLVSSLAASPVTRNYGRRASIVCG
SEQ ID NO:14                FFPSVFRKKNSDKTVNQYCQYDSQTLMFTSSLYLAALLSSLVASTVTRRFGRKXSMLFG
SEQ ID NO:16                ---------------------------TR----------------------------
SEQ ID NO:18                FFPEVYDKKQMKGSASQYCKYDNQLLQTFTSSLYLAALVSSFFLATVTRVVGRKWSMFTG
```

FIG. 1A

```
                                    121                                                          180
SEQ ID NO:19 (gi 1708191)  GXVFLAXAALGGAAVNVYMLIFGRVLLGVGVGFANQAVPLYLSEMAPPRYRGAINNGFQF
SEQ ID NO:20 (gi 347853)   ------------------------------------------------------------
SEQ ID NO:21 (gi 3540199)  SVSFFLGGVINAAAKNILMLILGRIFLGIGIFGVGFANQAVPLYLSEMAPAKIRGTVNQLFQL
SEQ ID NO:22 (gi 99758)    GFTFFIGSAFNGFAQNIAMLLIGRILLGRILLGFGVGFANQSVPVYLSEMAPPNLRGAFNNGFQV
SEQ ID NO:23 (gi 1353516)  GLLFLVGALINGFANHVWMLIVGRILLGFGIGFANQPVPLYLSEMAPYKYRGALNIGFQL
SEQ ID NO:24 (gi 4138724)  GLLFCAGAIINGAAKAVWMLIVGRILLGFGIGFANQSVPLYLSEMAPYKYRGALNIGFQL
SEQ ID NO:2                AASFFLGGAINGAAMNIAMLIVGRILLGVGVGFANQAVPVYLSEMAPARLRGMLNIGFQL
SEQ ID NO:4                GLTFLVGAALNGAAQDIAMLIVGRILLG--------------------------------
SEQ ID NO:6                ------------------------------------------------------------
SEQ ID NO:8                ------------------------------------------------------------
SEQ ID NO:10               GLTFLIGAALNGAAENVAMLIVGRILLGVGVGFATQSVPVYLSEMAPARLRGMLNIGFQL
SEQ ID NO:12               GLSFLAGATLNASAVNLVMLILGRILLGVGIRFGNQAVPLYLSEMAPAHLRGALNMMFQL
SEQ ID NO:14               GLLFLXGALINGFAXHVWXLIVGRILLGFGIRFANQSVPLXLSEMAPYKYRGALNIGFQL
SEQ ID NO:16               ------------------------------------------------------------
SEQ ID NO:18               GLTFLIGAALNGAAENIAMLIVGRILLGVGVGFANQSVPVYLSEMAPARLRGMLNIGFQL 181                                                          240
SEQ ID NO:19 (gi 1708191)  SVGIGALSANLINYGTEKIEGGWGWRISLAMAAVPAAILTFGALFLPETPNSLIQRSNDH
SEQ ID NO:20 (gi 347853)   ---------------------------------------------------IERGR-V
SEQ ID NO:21 (gi 3540199)  TTCIGILVANLINYKTEQIHP-WGWRLSLGLATVPAILMFLGGLVLPETPNSLVEQGK-L
SEQ ID NO:22 (gi 99758)    AIIFGIVVATINYFTAQMKGNIGWRISLGLACVPAVMIMIGALILPDTPNSLIERGY-T
SEQ ID NO:23 (gi 1353516)  SITIGILVANVLNYFFAKIKGGWGWRLSLGGAMVPALIITIGSLVLPDTPNSMIERGD-R
SEQ ID NO:24 (gi 4138724)  SITIGILVANILNYFFAKIKGGWGWRLSLGGAVVPALIITVGSLVLPDTPNSMIERGQ-H
SEQ ID NO:2                MITIGILAAELINYGTNKIKAGYGWRVSLALAAVPAAIITLGSLFLPDTPNSLLERGH-P
SEQ ID NO:4                ------------------------------------------------------------
SEQ ID NO:6                ------------------------------------------------------------
SEQ ID NO:8                ------------------------------------------------------------
SEQ ID NO:10               MITIGILAAELINYGTAKIKAGWGWRVSLALAAVPAAIITLGSLFLPDTPNSLIDRGH-P
SEQ ID NO:12               ATTLGIFTANMINYGTQHIRP-WGWRLSLGLAAAPALLMTVGGLLLPETPNSLIERGR-V
SEQ ID NO:14               SITVGILVANVLNYFFAKIKGGWGWRLSLGGAMVPALIITVGSLVLPDTPNSMIERGD-R
SEQ ID NO:16               ------------------------------------------------------------
SEQ ID NO:18               MITIGILAAALINYDTNKIKAGYGWRISLALAAVPAGIITLGSFFLPDTPNSLIERGH-P
```

FIG. 1B

```
                                    241                                                              300
SEQ ID NO:19  (gi 1708191)  ERAKIMLQRVRGTT-DVQAELDDLIKASIISRTIQHPFKNIMRRKYRPQLVMAVA-IPFF
SEQ ID NO:20  (gi  347853)  EEGRRVLERIRGTA-DVDAEFTDMVEASELANTIEHPFRNILEPRNRPQLVM-AVCMPAF
SEQ ID NO:21  (gi 3540199)  EKAKAVLIKVRGTN-NIEAEFQDLVEASDAARAVKNPFRNLLARRNRPQLVIGAIGLPAF
SEQ ID NO:22  (gi  997758)  EEAKEMLQSIRGTN-EVDEEFQDLIDASEESKQVKHPWKNIMLPRYRPQLIMTCF-IPFF
SEQ ID NO:23  (gi 1353516)  DGAKAQLKRIRGIE-DVDEEFNDLVAASEASMQVENPWRNLLQRKYRPQLTMAVL-IPFF
SEQ ID NO:24  (gi 4138724)  EGAKTKLRRIRGVD-DVEEEFNDLVVASEASKLVEHPWRNLLQRKYRPHLTMAIL-IPFF
SEQ ID NO:2                 EEAARRMLRRIRGTD-DIGEEYADLVAASEEARQVRHPWRNILRRYRAQLTMAVA-IPFF
SEQ ID NO:4                 ----------------------------------------------------------
SEQ ID NO:6                 ----------------------------------------------------------
SEQ ID NO:8                 ----------------------------------------------------------
SEQ ID NO:10                EAAERMLRRIRGSDVDVSEEYADIVAASED------------------------------
SEQ ID NO:12                EEGRRVLERIRGTA-DVDAEFTDMAEASELANSIEHPFRNILEPRNRPQLVM-AVCMPAF
SEQ ID NO:14                EKAKAQLQRIRGID-NVDEEFNDLVAASESSSQVEHPWRNLLQRKYRPHLTMAVL-IPFF
SEQ ID NO:16                ----------------------------------------------------------
SEQ ID NO:18                EAARRMLNRIRGSDVDISEEYADLVVASEESKLVQHPWRNILQRKYRPQLTMAIM-IPFF 301                                                              360
SEQ ID NO:19  (gi 1708191)  QQVTGINVIAFYAPILFRTIGLEESASLLSSIVTGLVGSASTFISMLIVDKLGRRALFIF
SEQ ID NO:20  (gi  347853)  QILTGINSILFYAPVLFQSMGFGGNASLYSSVLTGAVLFSSTLISIGTVDRLGRKLLIS
SEQ ID NO:21  (gi 3540199)  QQLTGMNSILFYAPVMFQSLGFGGSASLISSTITNAALVVAAIMSMYSADKFGRRFLLE
SEQ ID NO:22  (gi  997758)  QQLTGINVITFYAPVLFQTLGFGSKASLLSAMVTGIIELLCTFVSVFTVDRFGRRILFLQ
SEQ ID NO:23  (gi 1353516)  QQFTGINVIMFYAPVLFNSIGFKDDASLMSAVITGVVNVVATCVSIYGVDKWGRRALFLE
SEQ ID NO:24  (gi 4138724)  QQLTGINVIMFYAPVLFKTIGFADDASLMSAVITGGVNVLATIVSIYGVDKWGRRFLFLE
SEQ ID NO:2                 QQLKGINVIMFYAPVLFDTLGFKKEAFLMSSVITGLVNVFATVVSIVTVDRVGRRKLFLQ
SEQ ID NO:4                 ----------------------------------------------------------
SEQ ID NO:6                 ----------------------------------------------------------
SEQ ID NO:8                 ----------------------------------------------------------
SEQ ID NO:10                ----------------------------------------------------------
SEQ ID NO:12                ----------------------------------------------------------
SEQ ID NO:14                QILTGINSILFYAPVLFSSIGFKDDAALMSAVITGVVNVVATCVSIYGVDKWGRRALFLE
SEQ ID NO:16                ----------------------------------------------------------
SEQ ID NO:18                QQLTGINVIMFYAPVLFETLGFKGDASLMSAVITGLVNVFATLVSVFTVDRLGRRKLFLQ
```

FIG. 1C

```
                                361                                                           420
SEQ ID NO:19 (gi 17708191) GGVQMFVAQIMVGSIMAAELG---DHGGIGKGYAYIVLLICIYVAGFGWSWGPLGWLVP
SEQ ID NO:20 (gi 347853)   GGIQMIVCQVIVAVILGAKFGADK---QLSRSYSIAVVVICLFVLAFGWSWGPLGWTVP
SEQ ID NO:21 (gi 3540199)  ASVEMFCYMVVGVTLALKFGEGK---ELPKSLGLILVLLICLFVLAYGRSWGPMGWLVP
SEQ ID NO:22 (gi 99758)    GGIQMLVSQIAIGAMIGVKFGVAGT-GNIGKSDANLIVALICIYVAGFAWSWGPLGWLVP
SEQ ID NO:23 (gi 1353516)  GGAQMLICQVAVAAAIGAKFGTSGNPGNLPEWYAIVVVLFICIYVAGFAWSWGPLGWLVP
SEQ ID NO:24 (gi 4138724)  GGTQMLICQVIVATCIGVKFGVDGEPGALPKWYAIVVVLFICVYVSGFAWSWGPLGWLVP
SEQ ID NO:2                GGAQMIVCQLIVGTLIAAKFGTSGT-GDIAKGYAAVVVFICAYVAGFAWSWGPLGWLVP
SEQ ID NO:4                ---------------------------------A----R----A-----LTYLVP
SEQ ID NO:6                ------------------------------YAYLVLVIMXVFXAGFXWSGPLTYLVP
SEQ ID NO:8                ----------------------------------------------------------
SEQ ID NO:10               GGIQMIICQVIVAVILGVKFGTDK--ELTRSYSIAVVVICLFVLAFGWSWGPLGWTVP
SEQ ID NO:12               GGVQMLICQAVVAAAIGAKFGTDGNPGDLPKWYAIVVVLFICIYVSAFAWSWGPLGWLVP
SEQ ID NO:14               ---------------------------------------------------------P
SEQ ID NO:16               ----------------------------------------------------------
SEQ ID NO:18               GGTQMLLSQLVVGTLIAVKFGTSGV-GEMPKGYAAAVLFICLYVAGFAWSWGPLGWLVP 421                                                           480
SEQ ID NO:19 (gi 17708191) SEIFPLEIRSAGQSIVVAVSFLFTFVVAQTFLSMLCHFKSGIFFFGGWVVVMTAFVHFL
SEQ ID NO:20 (gi 347853)   SEIFPLETRSAGQSITVAVNLLFTFAIAQAFLSLLCAFKFGIFLFFAGWITVMTVFVCVF
SEQ ID NO:21 (gi 3540199)  SEIFPLETRSAGQSVVCVNLFFTALIAQCFLVSLCHLKYGIFLLFAGLLIGMGSFVYFL
SEQ ID NO:22 (gi 99758)    SEISPLEIRSAGQSAAQAINVSVNMFFTELVAQLFLTMLCHMKFGLFFFFAFFVVIMTIFIYLM
SEQ ID NO:23 (gi 1353516)  SEIFPLEIRSAAQSVNVSVNMLFTFLVAQVFLIMLCHMKFGLFLFFAFFVLVMSIYVFFL
SEQ ID NO:24 (gi 4138724)  SEIFPLEIRSAAQSINVSVNMFFTFIIAQIFLNMLCHMKFGLFLFFAFFVVMSFFIYFF
SEQ ID NO:2                SEIFPLEIRPAGQSINVSVNMFFTFCIAQAFLTMLCHFKFGLFYFFAGWVIMTVFIAFF
SEQ ID NO:4                TEICPLEIRSAGQSIVIAVIFFVTFLIGQTFLAMLCHLKFGTFFLFGGWVCVMTLFVYFF
SEQ ID NO:6                TEYLPX--IKSGXKSVVIAVIFFVTXIIGQTFLAMLXHLKFGTFFLFGGWVXXMXLFVXFF
SEQ ID NO:8                ------RTGAH
SEQ ID NO:10               SEIFPLETRSAGQSITVAVNLFFTFVIAQAFLSLLCALKFGIFLFFAGWITVMTVFVHVF
SEQ ID NO:12               SEIFPLEIRSAAQSINVSVNMLFTFLIAQVFLTMLCHMKFGLFLFFAFFVLIMTFFVYFF
SEQ ID NO:14               SELFPLEMRSAGQSVVVCVNLFWTAAVAQCFLAALCHLRWGVFVLFASLIVVMSIFVILL
SEQ ID NO:16               ---------CHLRWGVFVLFASLIVVMSIFVILL
SEQ ID NO:18               SEIFPLEIRPAGQSINVSVNMLFTFVIAQFITMLCHMKFGLFYFFAGWVIMTVFIALF
```

FIG. 1D

```
                                481                                                        532
SEQ ID NO:19  (gi 17081091)    LPETKKVPIEKMDIVWRDHWFWKKIIGEEA-AEENNKMEAA-------------
SEQ ID NO:20  (gi 347853)      LPETKGVPIEEMVLLWRKHWFWKKKVMPAD-----MPLEDGWGAAPASNNHK--
SEQ ID NO:21  (gi 3540199)     LPETKQVPIEEVYLLWRQHWLWKKYV-----------------EDVDE----
SEQ ID NO:22  (gi 997758)      LPETKNVPIEEMNRVWKAHWFWGKFIPD-----EAVNMGAAEMQQKSV□---
SEQ ID NO:23  (gi 1353516)     LPETKGIPIEEMDRVWKSHPFWSRFVEHGD-HGNGVEMGKG----APKNV--
SEQ ID NO:24  (gi 4138724)     LPETKGIPIEEMAEVWKSHWFWSRYVNDGS-YS-GVELVKENYPV--KNV--
SEQ ID NO:2                    LPETKNVPIEEMXLGWKXHWFWKRL-------------------SP------
SEQ ID NO:4                    ----------------------------------------------------
SEQ ID NO:6                    LPETKQLPMEQMEQVWRTHWFWKRIVDEDAAGEQPREEAAGTIALSSTSTTT
SEQ ID NO:8                    LXETKXLPMEXXEQXWRTHWXXKRIVDDDAGGEQPREEA-------------
SEQ ID NO:10                   ----------------------------------------------------
SEQ ID NO:12                   LPETKGVPIEEMVLLWRKHWFWKKKVMP-D-----LPLEDG-------DSHHK
SEQ ID NO:14                   LPETKGIPIEEMGQVWQAHPFWSRFVEHDD-YGNGVEMGKG----AIKEV--
SEQ ID NO:16                   LPETKQVPIEEIWMLFDKHWYWKRIVRRDPKYQGNLHQQQQQQQEMSKA---
SEQ ID NO:18                   LPETKNVPIEEMVLVWKGHWFWRRYIGDAD-VHVGANNGKGAAIA-------
```

FIG. 1E

SEQUENCE LISTING

<160> NUMBER OF SEQ ID NOS: 24

<210> SEQ ID NO 1
<211> LENGTH: 1675
<212> TYPE: DNA
<213> ORGANISM: Zea mays
<220> FEATURE:
<221> NAME/KEY: unsure
<222> LOCATION: (1624)
<223> OTHER INFORMATION: n = a, c, g or t
<220> FEATURE:
<221> NAME/KEY: unsure
<222> LOCATION: (1638)
<223> OTHER INFORMATION: n = a, c, g or t
<220> FEATURE:
<221> NAME/KEY: unsure
<222> LOCATION: (1668)
<223> OTHER INFORMATION: n = a, c, g or t
<220> FEATURE:
<221> NAME/KEY: unsure
<222> LOCATION: (1670)
<223> OTHER INFORMATION: n = a, c, g or t
<220> FEATURE:
<221> NAME/KEY: unsure
<222> LOCATION: (1674)
<223> OTHER INFORMATION: n = a, c, g or t

<400> SEQUENCE: 1

```
ctgccctgcg cccctgccta tttcattcct cctctcccct ccctgccta tttcattctt      60
tgtttgtttc agcctttcac ggaagagggg cggagtacgt aaggtgaacc cggtcgtctg    120
aagagaagcg agcacgacgt aggagagggg aggacagcga gatggccggc gggtttggcg    180
gcggcgggc agccgccggg agggccgagc tctacgaggg caagatcacc ggctacttca    240
tcctcgcttg catcgtcggc tccttcggcg gatccctctt cggctatgac ctcggagtct    300
ccagcggcgt gacttccatg gacgacttcc tggtgaagtt cttcccggac gtgtaccggc    360
ggaagcaggc gcacctgcac gagacggact actgcaagta cgacaaccag gtgctgacgc    420
tcttcacctc gtcgctctac ttcgcgggcc tcgtctccac cttcggcgcc tcctacgtga    480
ccaagcgcca cggccggcgc gccagcatca tgggtggcgc cgccagcttc ttcctcggcg    540
gcgccatcaa cggcgccgcc atgaacatcg ccatgctcat cgtcggacgc atcctcctcg    600
gcgtcggcgt cggcttcgca aatcaggccg tgcctgtgta cctgtcggag atggcgccgg    660
cgcgtctccg gggcatgctc aacatcggct tccagctgat gatcaccatc ggcatcctgg    720
cggcggagct catcaactac ggcaccaaca agatcaaggc cgggtacggg tggcgcgtga    780
gcctggcgct ggcggcggtg ccggcggcca tcatcaccct gggctccctc ttcctcccgg    840
acacccccaa ctcgctgctg gagcggggcc accggagga ggcacgccgc atgctccgcc    900
gcatccgcgg cacggacgac atcggcgagg agtacgcgga cctggtggcg gccagcgagg    960
aggcccgcca ggtgcgccac ccgtggcgga acatcctgcg ccgccggtac cgcgcgcagc   1020
tcaccatggc cgtcgcgatc cccttcttcc agcagctcaa ggggatcaac gtcatcatgt   1080
tctacgcgcc cgtgctgttc gacacgctgg gattcaagaa agaagccttc ctcatgtcct   1140
ccgtcatcac gggcctcgtc aacgtcttcg ccaccgtcgt gtccatcgtc accgtcgacc   1200
gcgtcggccg ccgcaagctg ttcctccagg gcggcgcgca gatgatcgtg tgccagctca   1260
tcgtgggcac gctcatcgcc gccaagttcg ggaccagcgg cacggggac atcgccaagg   1320
gctacgccgc ggtcgtcgtg gtcttcatct gcgcctacgt cgccggcttc gcctggtcgt   1380
gggggcccct gggctggctc gtgccgtccg agatcttccc gctggagatc cgcccggcgg   1440
```

```
ggcagagcat caacgtctcc gtcaacatgt tcttcacctt ctgcatcgcg caggccttcc   1500
tcaccatgct ctgccacttc aagttcggcc tcttctactt cttcgccggc tgggtcgtca   1560
tcatgaccgt ctttatcgcc ttcttcctgc ccgagaccaa gaacgtgccc atcgaggaga   1620
tggngcttgg ctggaagnca cactggttct ggaaaaggtt atcgccgncn aagnc        1675
```

<210> SEQ ID NO 2
<211> LENGTH: 502
<212> TYPE: PRT
<213> ORGANISM: Zea mays
<220> FEATURE:
<221> NAME/KEY: UNSURE
<222> LOCATION: (488)
<223> OTHER INFORMATION: Xaa = any amino acid
<220> FEATURE:
<221> NAME/KEY: UNSURE
<222> LOCATION: (493)
<223> OTHER INFORMATION: Xaa = any amino acid

<400> SEQUENCE: 2

```
Met Ala Gly Gly Phe Gly Gly Gly Ala Ala Ala Gly Arg Ala Glu
 1               5                  10                  15

Leu Tyr Glu Gly Lys Ile Thr Gly Tyr Phe Ile Leu Ala Cys Ile Val
                20                  25                  30

Gly Ser Phe Gly Gly Ser Leu Phe Gly Tyr Asp Leu Gly Val Ser Ser
            35                  40                  45

Gly Val Thr Ser Met Asp Asp Phe Leu Val Lys Phe Phe Pro Asp Val
        50                  55                  60

Tyr Arg Arg Lys Gln Ala His Leu His Glu Thr Asp Tyr Cys Lys Tyr
 65                  70                  75                  80

Asp Asn Gln Val Leu Thr Leu Phe Thr Ser Ser Leu Tyr Phe Ala Gly
                85                  90                  95

Leu Val Ser Thr Phe Gly Ala Ser Tyr Val Thr Lys Arg His Gly Arg
            100                 105                 110

Arg Ala Ser Ile Met Gly Gly Ala Ala Ser Phe Phe Leu Gly Gly Ala
        115                 120                 125

Ile Asn Gly Ala Ala Met Asn Ile Ala Met Leu Ile Val Gly Arg Ile
130                 135                 140

Leu Leu Gly Val Gly Val Gly Phe Ala Asn Gln Ala Val Pro Val Tyr
145                 150                 155                 160

Leu Ser Glu Met Ala Pro Ala Arg Leu Arg Gly Met Leu Asn Ile Gly
                165                 170                 175

Phe Gln Leu Met Ile Thr Ile Gly Ile Leu Ala Ala Glu Leu Ile Asn
            180                 185                 190

Tyr Gly Thr Asn Lys Ile Lys Ala Gly Tyr Gly Trp Arg Val Ser Leu
        195                 200                 205

Ala Leu Ala Ala Val Pro Ala Ala Ile Ile Thr Leu Gly Ser Leu Phe
    210                 215                 220

Leu Pro Asp Thr Pro Asn Ser Leu Leu Glu Arg Gly His Pro Glu Glu
225                 230                 235                 240

Ala Arg Arg Met Leu Arg Arg Ile Arg Gly Thr Asp Asp Ile Gly Glu
                245                 250                 255

Glu Tyr Ala Asp Leu Val Ala Ala Ser Glu Glu Ala Arg Gln Val Arg
            260                 265                 270

His Pro Trp Arg Asn Ile Leu Arg Arg Arg Tyr Arg Ala Gln Leu Thr
        275                 280                 285
```

```
Met Ala Val Ala Ile Pro Phe Gln Gln Leu Lys Gly Ile Asn Val
    290                 295                 300

Ile Met Phe Tyr Ala Pro Val Leu Phe Asp Thr Leu Gly Phe Lys Lys
305                 310                 315                 320

Glu Ala Phe Leu Met Ser Ser Val Ile Thr Gly Leu Val Asn Val Phe
                325                 330                 335

Ala Thr Val Val Ser Ile Val Thr Val Asp Arg Val Gly Arg Arg Lys
                340                 345                 350

Leu Phe Leu Gln Gly Gly Ala Gln Met Ile Val Cys Gln Leu Ile Val
            355                 360                 365

Gly Thr Leu Ile Ala Ala Lys Phe Gly Thr Ser Gly Thr Gly Asp Ile
    370                 375                 380

Ala Lys Gly Tyr Ala Ala Val Val Val Phe Ile Cys Ala Tyr Val
385                 390                 395                 400

Ala Gly Phe Ala Trp Ser Trp Gly Pro Leu Gly Trp Leu Val Pro Ser
                405                 410                 415

Glu Ile Phe Pro Leu Glu Ile Arg Pro Ala Gly Gln Ser Ile Asn Val
                420                 425                 430

Ser Val Asn Met Phe Phe Thr Phe Cys Ile Ala Gln Ala Phe Leu Thr
                435                 440                 445

Met Leu Cys His Phe Lys Phe Gly Leu Phe Tyr Phe Phe Ala Gly Trp
    450                 455                 460

Val Val Ile Met Thr Val Phe Ile Ala Phe Phe Leu Pro Glu Thr Lys
465                 470                 475                 480

Asn Val Pro Ile Glu Glu Met Xaa Leu Gly Trp Lys Xaa His Trp Phe
                485                 490                 495

Trp Lys Arg Leu Ser Pro
            500

<210> SEQ ID NO 3
<211> LENGTH: 517
<212> TYPE: DNA
<213> ORGANISM: Zea mays

<400> SEQUENCE: 3
gcacgagaga agctgtccct ccctccctcc ctcccctgtg cttctgctag ctagctaggt      60
gcctgccgag gagagatagg gatacgatgg ccggcggtgg catcgtgaac acgggcggtg     120
gcaaggacta ccccggcaag ctcacccctct tcgtgttgct cacctgcatc gtcgccgcca    180
ccggcggtct catcttcgga tatgacatcg gtatctcagg cggcgtgacg tccatgaacc    240
cgttcctgga gaagttcttc ccggaggtgt accggaagaa gcaggaggcc aagacgaacc    300
agtactgcaa gtacgacaac cagctgctgc agaccttcac ctcctccctc tacctggccg    360
cgctggtcgc ctccttcttc gccgccaccg tcacccgcgc cgtcggccgc aagtggtcca    420
tgctcgtcgg gggcctcacc ttcctcgtcg gcgccgccct caacggcgcc gcccaggaca    480
tcgccatgct catcgtcgga cgcatcctcc tcggcgt                              517

<210> SEQ ID NO 4
<211> LENGTH: 143
<212> TYPE: PRT
<213> ORGANISM: Zea mays

<400> SEQUENCE: 4

Met Ala Gly Gly Gly Ile Val Asn Thr Gly Gly Gly Lys Asp Tyr Pro
  1               5                  10                  15
```

```
Gly Lys Leu Thr Leu Phe Val Leu Thr Cys Ile Val Ala Ala Thr
             20                  25                  30
Gly Gly Leu Ile Phe Gly Tyr Asp Ile Gly Ile Ser Gly Val Thr
         35                  40                  45
Ser Met Asn Pro Phe Leu Glu Lys Phe Phe Pro Glu Val Tyr Arg Lys
 50                  55                  60
Lys Gln Glu Ala Lys Thr Asn Gln Tyr Cys Lys Tyr Asp Asn Gln Leu
 65                  70                  75                  80
Leu Gln Thr Phe Thr Ser Ser Leu Tyr Leu Ala Ala Leu Val Ala Ser
                 85                  90                  95
Phe Phe Ala Ala Thr Val Thr Arg Ala Val Gly Arg Lys Trp Ser Met
             100                 105                 110
Leu Val Gly Gly Leu Thr Phe Leu Val Gly Ala Ala Leu Asn Gly Ala
         115                 120                 125
Ala Gln Asp Ile Ala Met Leu Ile Val Gly Arg Ile Leu Leu Gly
     130                 135                 140
```

<210> SEQ ID NO 5
<211> LENGTH: 542
<212> TYPE: DNA
<213> ORGANISM: Zea mays

<400> SEQUENCE: 5

```
gcacgagctc tcacctacct ggtgcccacc gagatctgcc cgctggagat caggtcggcg    60
gggcagagcg tcgtcatcgc cgtcatcttc ttcgtcacct tcctcatcgg ccagaccttc   120
ctggcgatgc tgtgccacct caagttcggc accttcttcc tcttcggcgg ctgggtgtgc   180
gtcatgacgc tcttcgtgta tttcttcctg ccggagacca agcagctgcc catggagcag   240
atggaacagg tctggaggac ccactggttt tggaaaagga ttgtagacga agatgcagca   300
ggggagcaac cgagagagga agcagcagga accatagctc tgtcgtccac gtccaccaca   360
acatagtcat catcaacaat actcatggca tgggcctgcc ctgtatagat agataattaa   420
ctagctgcac cgcacagatt gtctccgact ataagctagc tagctagttg gatgcatgca   480
tgcatgcatt ctgttatttc tgtgaccatg aatcaaaggg ccttccaaca aaaaaaaaa   540
aa                                                                  542
```

<210> SEQ ID NO 6
<211> LENGTH: 121
<212> TYPE: PRT
<213> ORGANISM: Zea mays

<400> SEQUENCE: 6

```
Ala Arg Ala Leu Thr Tyr Leu Val Pro Thr Glu Ile Cys Pro Leu Glu
 1               5                  10                  15
Ile Arg Ser Ala Gly Gln Ser Val Val Ile Ala Val Ile Phe Phe Val
             20                  25                  30
Thr Phe Leu Ile Gly Gln Thr Phe Leu Ala Met Leu Cys His Leu Lys
         35                  40                  45
Phe Gly Thr Phe Phe Leu Phe Gly Gly Trp Val Cys Val Met Thr Leu
 50                  55                  60
Phe Val Tyr Phe Phe Leu Pro Glu Thr Lys Gln Leu Pro Met Glu Gln
 65                  70                  75                  80
Met Glu Gln Val Trp Arg Thr His Trp Phe Trp Lys Arg Ile Val Asp
                 85                  90                  95
Glu Asp Ala Ala Gly Glu Gln Pro Arg Glu Glu Ala Ala Gly Thr Ile
```

-continued

```
                    100                 105                 110
Ala Leu Ser Ser Thr Ser Thr Thr Thr
            115                 120

<210> SEQ ID NO 7
<211> LENGTH: 593
<212> TYPE: DNA
<213> ORGANISM: Zea mays
<220> FEATURE:
<221> NAME/KEY: unsure
<222> LOCATION: (32)
<223> OTHER INFORMATION: n = a, c, g or t
<220> FEATURE:
<221> NAME/KEY: unsure
<222> LOCATION: (40)
<223> OTHER INFORMATION: n = a, c, g or t
<220> FEATURE:
<221> NAME/KEY: unsure
<222> LOCATION: (52)
<223> OTHER INFORMATION: n = a, c, g or t
<220> FEATURE:
<221> NAME/KEY: unsure
<222> LOCATION: (103)
<223> OTHER INFORMATION: n = a, c, g or t
<220> FEATURE:
<221> NAME/KEY: unsure
<222> LOCATION: (123)
<223> OTHER INFORMATION: n = a, c, g or t
<220> FEATURE:
<221> NAME/KEY: unsure
<222> LOCATION: (162)
<223> OTHER INFORMATION: n = a, c, g or t
<220> FEATURE:
<221> NAME/KEY: unsure
<222> LOCATION: (172)
<223> OTHER INFORMATION: n = a, c, g or t
<220> FEATURE:
<221> NAME/KEY: unsure
<222> LOCATION: (195)
<223> OTHER INFORMATION: n = a, c, g or t
<220> FEATURE:
<221> NAME/KEY: unsure
<222> LOCATION: (240)
<223> OTHER INFORMATION: n = a, c, g or t
<220> FEATURE:
<221> NAME/KEY: unsure
<222> LOCATION: (242)
<223> OTHER INFORMATION: n = a, c, g or t
<220> FEATURE:
<221> NAME/KEY: unsure
<222> LOCATION: (249)
<223> OTHER INFORMATION: n = a, c, g or t
<220> FEATURE:
<221> NAME/KEY: unsure
<222> LOCATION: (261)
<223> OTHER INFORMATION: n = a, c, g or t
<220> FEATURE:
<221> NAME/KEY: unsure
<222> LOCATION: (272)
<223> OTHER INFORMATION: n = a, c, g or t
<220> FEATURE:
<221> NAME/KEY: unsure
<222> LOCATION: (299)
<223> OTHER INFORMATION: n = a, c, g or t
<220> FEATURE:
<221> NAME/KEY: unsure
<222> LOCATION: (304)
<223> OTHER INFORMATION: n = a, c, g or t
<220> FEATURE:
<221> NAME/KEY: unsure
<222> LOCATION: (311)
<223> OTHER INFORMATION: n = a, c, g or t
<220> FEATURE:
<221> NAME/KEY: unsure
<222> LOCATION: (329)
<223> OTHER INFORMATION: n = a, c, g or t
<220> FEATURE:
```

```
<221> NAME/KEY: unsure
<222> LOCATION: (332)
<223> OTHER INFORMATION: n = a, c, g or t
<220> FEATURE:
<221> NAME/KEY: unsure
<222> LOCATION: (399)
<223> OTHER INFORMATION: n = a, c, g or t
<220> FEATURE:
<221> NAME/KEY: unsure
<222> LOCATION: (414)
<223> OTHER INFORMATION: n = a, c, g or t
<220> FEATURE:
<221> NAME/KEY: unsure
<222> LOCATION: (422)
<223> OTHER INFORMATION: n = a, c, g or t
<220> FEATURE:
<221> NAME/KEY: unsure
<222> LOCATION: (443)
<223> OTHER INFORMATION: n = a, c, g or t
<220> FEATURE:
<221> NAME/KEY: unsure
<222> LOCATION: (445)
<223> OTHER INFORMATION: n = a, c, g or t
<220> FEATURE:
<221> NAME/KEY: unsure
<222> LOCATION: (463)
<223> OTHER INFORMATION: n = a, c, g or t
<220> FEATURE:
<221> NAME/KEY: unsure
<222> LOCATION: (495)
<223> OTHER INFORMATION: n = a, c, g or t
<220> FEATURE:
<221> NAME/KEY: unsure
<222> LOCATION: (507)
<223> OTHER INFORMATION: n = a, c, g or t
<220> FEATURE:
<221> NAME/KEY: unsure
<222> LOCATION: (518)
<223> OTHER INFORMATION: n = a, c, g or t
<220> FEATURE:
<221> NAME/KEY: unsure
<222> LOCATION: (525)
<223> OTHER INFORMATION: n = a, c, g or t
<220> FEATURE:
<221> NAME/KEY: unsure
<222> LOCATION: (544)..(545)
<223> OTHER INFORMATION: n = a, c, g or t
<220> FEATURE:
<221> NAME/KEY: unsure
<222> LOCATION: (563)
<223> OTHER INFORMATION: n = a, c, g or t
<220> FEATURE:
<221> NAME/KEY: unsure
<222> LOCATION: (577)..(578)
<223> OTHER INFORMATION: n = a, c, g or t
<220> FEATURE:
<221> NAME/KEY: unsure
<222> LOCATION: (581)
<223> OTHER INFORMATION: n = a, c, g or t

<400> SEQUENCE: 7
agtacgcgta cctggtgctc gtcatcatgt gngtcttcgn cgcgggcttc gnctggtcct      60
ggggccctct cacctacctg gtgcccaccg agtatctgcc cgntggagga tcaagtcggg     120
ggngaagagc gtcgtcatcg ccgtcatctt cttcgtcacc tncatcatcg gncagacctt     180
cctggcgatg ctgtnccacc tcaagttcgg caccttcttc ctcttcgggg gatgggtgtn     240
cntcatgang ctcttcgtgt ntttcttcct gncggagacc aagtagctgc ccatggagna     300
gatngaacag ntctggagga cccactgggng tnggaaaagg attgtagacg atgatgcagg     360
aggggagcaa ccgagagagg aagcagtagg aaccattgnt ctgtcgtcca cgtncaccac     420
ancataggtc atccatcaaa cantnctcat gggatgggcc ctngccctgt tttagataga     480
ttatttaact agctncaccc aaacagnttg cctcctanta taagnctagc ttagcttagt     540
```
tggnntgaat acatgaatgc atnctgtctt tcccttnncc naccataaat caa          593

<210> SEQ ID NO 8
<211> LENGTH: 126
<212> TYPE: PRT
<213> ORGANISM: Zea mays
<220> FEATURE:
<221> NAME/KEY: UNSURE
<222> LOCATION: (10)
<223> OTHER INFORMATION: Xaa = any amino acid
<220> FEATURE:
<221> NAME/KEY: UNSURE
<222> LOCATION: (13)
<223> OTHER INFORMATION: Xaa = any amino acid
<220> FEATURE:
<221> NAME/KEY: UNSURE
<222> LOCATION: (17)
<223> OTHER INFORMATION: Xaa = any amino acid
<220> FEATURE:
<221> NAME/KEY: UNSURE
<222> LOCATION: (34)
<223> OTHER INFORMATION: Xaa = any amino acid
<220> FEATURE:
<221> NAME/KEY: UNSURE
<222> LOCATION: (39)
<223> OTHER INFORMATION: Xaa = any amino acid
<220> FEATURE:
<221> NAME/KEY: UNSURE
<222> LOCATION: (52)
<223> OTHER INFORMATION: Xaa = any amino acid
<220> FEATURE:
<221> NAME/KEY: UNSURE
<222> LOCATION: (63)
<223> OTHER INFORMATION: Xaa = any amino acid
<220> FEATURE:
<221> NAME/KEY: UNSURE
<222> LOCATION: (78)..(79)
<223> OTHER INFORMATION: Xaa = any amino acid
<220> FEATURE:
<221> NAME/KEY: UNSURE
<222> LOCATION: (81)
<223> OTHER INFORMATION: Xaa = any amino acid
<220> FEATURE:
<221> NAME/KEY: UNSURE
<222> LOCATION: (85)
<223> OTHER INFORMATION: Xaa = any amino acid
<220> FEATURE:
<221> NAME/KEY: UNSURE
<222> LOCATION: (89)
<223> OTHER INFORMATION: Xaa = any amino acid
<220> FEATURE:
<221> NAME/KEY: UNSURE
<222> LOCATION: (93)
<223> OTHER INFORMATION: Xaa = any amino acid
<220> FEATURE:
<221> NAME/KEY: UNSURE
<222> LOCATION: (98)..(99)
<223> OTHER INFORMATION: Xaa = any amino acid
<220> FEATURE:
<221> NAME/KEY: UNSURE
<222> LOCATION: (102)
<223> OTHER INFORMATION: Xaa = any amino acid
<220> FEATURE:
<221> NAME/KEY: UNSURE
<222> LOCATION: (108)..(109)
<223> OTHER INFORMATION: Xaa = any amino acid

<400> SEQUENCE: 8

Tyr Ala Tyr Leu Val Leu Val Ile Met Xaa Val Phe Xaa Ala Gly Phe
 1               5                  10                  15

Xaa Trp Ser Trp Gly Pro Leu Thr Tyr Leu Val Pro Thr Glu Tyr Leu
             20                  25                  30

Pro Xaa Ile Lys Ser Gly Xaa Lys Ser Val Val Ile Ala Val Ile Phe
         35                  40                  45

-continued

```
Phe Val Thr Xaa Ile Ile Gly Gln Thr Phe Leu Ala Met Leu Xaa His
         50                  55                  60

Leu Lys Phe Gly Thr Phe Phe Leu Phe Gly Gly Trp Val Xaa Xaa Met
 65                  70                  75                  80

Xaa Leu Phe Val Xaa Phe Phe Leu Xaa Glu Thr Lys Xaa Leu Pro Met
                 85                  90                  95

Glu Xaa Xaa Glu Gln Xaa Trp Arg Thr His Trp Xaa Xaa Lys Arg Ile
            100                 105                 110

Val Asp Asp Ala Gly Gly Glu Gln Pro Arg Glu Glu Ala
        115                 120                 125
```

<210> SEQ ID NO 9
<211> LENGTH: 1167
<212> TYPE: DNA
<213> ORGANISM: Oryza sativa
<220> FEATURE:
<221> NAME/KEY: unsure
<222> LOCATION: (1020)
<223> OTHER INFORMATION: n = a, c, g or t
<220> FEATURE:
<221> NAME/KEY: unsure
<222> LOCATION: (1031)
<223> OTHER INFORMATION: n = a, c, g or t
<220> FEATURE:
<221> NAME/KEY: unsure
<222> LOCATION: (1059)
<223> OTHER INFORMATION: n = a, c, g or t
<220> FEATURE:
<221> NAME/KEY: unsure
<222> LOCATION: (1086)
<223> OTHER INFORMATION: n = a, c, g or t
<220> FEATURE:
<221> NAME/KEY: unsure
<222> LOCATION: (1126)
<223> OTHER INFORMATION: n = a, c, g or t

<400> SEQUENCE: 9

```
gcacgaggtt ctaacgatcg atcgattgct tctccctcct ctcgctacta gactagagag     60
taggtagagc tagcttttcta gctcgtggat cgttaagttt gtagtcctgc ccgggcgccg   120
gcggtgaggt cgcgatggcc ggcggcgcgg tggtgagcac gggggcaggc aaggactacc   180
ctggcaagct caccctcttc gtcttcttca catgcgtcgt cgccgccacc ggtggtctca   240
tcttcggata tgacatcggt atatcaggtg gtgtgacgtc catggacccg ttcctgagga   300
agttcttccc ggaggtgtat cggaagaagc agatggcgga caagaacaac cagtactgca   360
agtacgacaa ccagctgctg cagaccttca cctcgtcgct ctacctcgcc gccctcgtct   420
cctccttctt cgccgccacc gtcacccgcg tcctcggccg caagtggtcc atgttcgccg   480
gcggcctcac cttcctcatc ggcgccgccc tcaacggcgc cgccgagaac gtcgccatgc   540
tcatcgtcgg tcgtatcctc ctcggtgtcg cgtcggctt cgccactcag tcggtgccgg   600
tgtacttgtc ggagatggcg ccggctcggc tgcgggggat gctgaacatc gggttccagc   660
tgatgatcac catcggcatc ctggcggcgg agctgataaa ctacgggacg gcgaagatca   720
aggccgggtg gggatggcgg gtgagcctgg cgctggccgc cgtccccgcc gccatcatca   780
ccctcggctc cctcttcctc ccggacaccc ccaactcgct catcgacagg gccacccgg    840
aggcggcgga gcgcatgctc cggcgcatcc gcggctccga cgtggacgtg tcggaggagt   900
acgcggacct ggtggcggcg agcgaggatc gaactggtgc acaccgtggc caacactccg   960
ccgcaatacc gcgccaactc acatggcatc tgcatccctc tcaacactca cgggatcaan  1020
tctatgttca ngcccgtgct tcacacctgg gttaagagna cctcctattc gcgtcatacg  1080
```

```
gctctnaact ctcgcacgcg ggtcatctca cgtgacgctc gcgcgnactg tctgaaggcg      1140
gggccaaatg tgtttcagtg tgtggga                                           1167
```

<210> SEQ ID NO 10
<211> LENGTH: 270
<212> TYPE: PRT
<213> ORGANISM: Oryza sativa

<400> SEQUENCE: 10

```
Met Ala Gly Gly Ala Val Val Ser Thr Gly Ala Gly Lys Asp Tyr Pro
 1               5                  10                  15

Gly Lys Leu Thr Leu Phe Val Phe Thr Cys Val Val Ala Ala Thr
                20                  25                  30

Gly Gly Leu Ile Phe Gly Tyr Asp Ile Gly Ile Ser Gly Gly Val Thr
            35                  40                  45

Ser Met Asp Pro Phe Leu Arg Lys Phe Phe Pro Glu Val Tyr Arg Lys
 50                  55                  60

Lys Gln Met Ala Asp Lys Asn Asn Gln Tyr Cys Lys Tyr Asp Asn Gln
 65                  70                  75                  80

Leu Leu Gln Thr Phe Thr Ser Ser Leu Tyr Leu Ala Ala Leu Val Ser
                85                  90                  95

Ser Phe Phe Ala Ala Thr Val Thr Arg Val Leu Gly Arg Lys Trp Ser
               100                 105                 110

Met Phe Ala Gly Gly Leu Thr Phe Leu Ile Gly Ala Ala Leu Asn Gly
           115                 120                 125

Ala Ala Glu Asn Val Ala Met Leu Ile Val Gly Arg Ile Leu Leu Gly
130                 135                 140

Val Gly Val Gly Phe Ala Thr Gln Ser Val Pro Val Tyr Leu Ser Glu
145                 150                 155                 160

Met Ala Pro Ala Arg Leu Arg Gly Met Leu Asn Ile Gly Phe Gln Leu
               165                 170                 175

Met Ile Thr Ile Gly Ile Leu Ala Ala Glu Leu Ile Asn Tyr Gly Thr
           180                 185                 190

Ala Lys Ile Lys Ala Gly Trp Gly Trp Arg Val Ser Leu Ala Leu Ala
       195                 200                 205

Ala Val Pro Ala Ala Ile Ile Thr Leu Gly Ser Leu Phe Leu Pro Asp
210                 215                 220

Thr Pro Asn Ser Leu Ile Asp Arg Gly His Pro Glu Ala Ala Glu Arg
225                 230                 235                 240

Met Leu Arg Arg Ile Arg Gly Ser Asp Val Asp Val Ser Glu Glu Tyr
               245                 250                 255

Ala Asp Leu Val Ala Ala Ser Glu Asp Arg Thr Gly Ala His
           260                 265                 270
```

<210> SEQ ID NO 11
<211> LENGTH: 1776
<212> TYPE: DNA
<213> ORGANISM: Oryza sativa
<220> FEATURE:
<221> NAME/KEY: unsure
<222> LOCATION: (66)
<223> OTHER INFORMATION: n = a, c, g or t
<220> FEATURE:
<221> NAME/KEY: unsure
<222> LOCATION: (219)
<223> OTHER INFORMATION: n = a, c, g or t

<400> SEQUENCE: 11

-continued

```
gttctaacga gatagccata tcttcgctgt gcgtcgtcgt cgtcgctgcg tggtgaattc      60
ttgggngagg aggaggacga gatggcggga ggcggcgtgg cggcgctggg ggtgaagaag     120
gagcgggcgg cggagtacaa gggccgcatg acgctcgccg tcggcatggc ctgcctcgtc     180
gccgccgtcg gcggcgccat cttcggctac gacatcggna tctccggggg agtgacgtcc     240
atggatccgt tcctcaagaa gttcttcccg gtggtgttcc ggaagaagaa cgacgacggc     300
cagaacaact actgcaagta cgacaaccag ggcctctcgg cgttcacctc ctccctctac     360
ctcgccggcc tcgtctcctc ccttgccgcc tcgccggtga cgaggaacta cggccgccgc     420
gccagcatcg tctgcggcgg cctcagcttc ctcgccggcg ccacgctcaa cgcctccgcc     480
gttaacctcg tcatgctcat cctcggccgc atcctgctcg cgtcggaat  ccgcttcggc     540
aaccaggccg tgccgctgta cctgtcggaa atggcgccgg cgcacctccg cggcgcgctg     600
aacatgatgt tccagctggc gacgacgctg ggcatcttca cggcgaacat gatcaactac     660
gggacgcagc acatcaggcc gtgggggtgg cggctctcgc tggggctcgc ggcggcgccg     720
gcgctgctga tgaccgtcgg cgggctgctc ctgccggaga cgcccaacag cctgatcgag     780
cgcgggcgcg tcgaggaggg ccgccgcgtg ctggagcgca tccggggcac cgccgacgtg     840
gacgccgagt tcacggacat ggcggaggcg agcgagctcg ccaactccat cgagcacccg     900
ttccgcaaca tcctggagcc gcgcaaccgg ccgcagctgg tgatggcggt gtgcatgccg     960
gcgttccaga tcctgacggg catcaactcc atcctcttct acgcgcccgt gctgttccag    1020
agcatgggct tcggcggcag cgcgtcgctc tactcctcag tcctcaccgg cgccgtcctc    1080
ttctcctcca ccatcatctc catctccacc gtcgaccgcc tcggccgccg caagctcctc    1140
atcagcggcg gcatccaaat gatcatctgc caggtgatag tggcggtgat cttgggggtg    1200
aagttcggga cggacaagga gctgacgagg agctactcga tcgcggtggt ggtggtgatc    1260
tgcctgttcg tgctggcgtt cgggtggtcg tggggccgc  tggggtggac ggtgccgagc    1320
gagatcttcc gctggagac  gaggtcggcg gggcagagca tcacggtggc ggtgaacctc    1380
ttcttcacct tcgtcatcgc gcaggcgttc ctgtccctgc tctgcgcgct caagttcggc    1440
atcttcctct tcttcgccgg gtggatcacc gtcatgaccg tcttcgtcca cgtcttcctg    1500
ccggagacca agggcgtgcc catcgaggag atggtgctcc tatggaggaa gcactggttc    1560
tggaagaagg tcatgcccga cctgccgctc gaggacggcg acagtcatca aagtgaaag    1620
aaatgtactc tgagatagta tatgggggtt acagtagatg agacatgaca tgtaggatga    1680
ggagattaag attgatcatg tgcggtaatg cattctgtgt gtatgttaat tgaagttcat    1740
ggatcaaaaa aaaaaaaaaa aaaaaaaaaa aaaaaa                               1776
```

<210> SEQ ID NO 12
<211> LENGTH: 511
<212> TYPE: PRT
<213> ORGANISM: Oryza sativa

<400> SEQUENCE: 12

```
Met Ala Gly Gly Gly Val Ala Ala Leu Gly Val Lys Lys Glu Arg Ala
  1               5                  10                  15

Ala Glu Tyr Lys Gly Arg Met Thr Leu Ala Val Gly Met Ala Cys Leu
             20                  25                  30

Val Ala Ala Val Gly Gly Ala Ile Phe Gly Tyr Asp Ile Gly Ile Ser
         35                  40                  45

Gly Gly Val Thr Ser Met Asp Pro Phe Leu Lys Lys Phe Phe Pro Val
```

-continued

```
                 50                       55                       60
Val Phe Arg Lys Lys Asn Asp Asp Gly Gln Asn Asn Tyr Cys Lys Tyr
 65                      70                       75                      80

Asp Asn Gln Gly Leu Ser Ala Phe Thr Ser Ser Leu Tyr Leu Ala Gly
                         85                       90                       95

Leu Val Ser Ser Leu Ala Ala Ser Pro Val Thr Arg Asn Tyr Gly Arg
                        100                      105                      110

Arg Ala Ser Ile Val Cys Gly Gly Leu Ser Phe Leu Ala Gly Ala Thr
                        115                      120                      125

Leu Asn Ala Ser Ala Val Asn Leu Val Met Leu Ile Leu Gly Arg Ile
                130                      135                      140

Leu Leu Gly Val Gly Ile Arg Phe Gly Asn Gln Ala Val Pro Leu Tyr
145                      150                      155                      160

Leu Ser Glu Met Ala Pro Ala His Leu Arg Gly Ala Leu Asn Met Met
                         165                      170                      175

Phe Gln Leu Ala Thr Thr Leu Gly Ile Phe Thr Ala Asn Met Ile Asn
                         180                      185                      190

Tyr Gly Thr Gln His Ile Arg Pro Trp Gly Trp Arg Leu Ser Leu Gly
                         195                      200                      205

Leu Ala Ala Pro Ala Leu Leu Met Thr Val Gly Gly Leu Leu Leu
210                      215                      220

Pro Glu Thr Pro Asn Ser Leu Ile Glu Arg Gly Arg Val Glu Glu Gly
225                      230                      235                      240

Arg Arg Val Leu Glu Arg Ile Arg Gly Thr Ala Asp Val Asp Ala Glu
                        245                      250                      255

Phe Thr Asp Met Ala Glu Ala Ser Glu Leu Ala Asn Ser Ile Glu His
                260                      265                      270

Pro Phe Arg Asn Ile Leu Glu Pro Arg Asn Arg Pro Gln Leu Val Met
                275                      280                      285

Ala Val Cys Met Pro Ala Phe Gln Ile Leu Thr Gly Ile Asn Ser Ile
                290                      295                      300

Leu Phe Tyr Ala Pro Val Leu Phe Gln Ser Met Gly Phe Gly Gly Ser
305                      310                      315                      320

Ala Ser Leu Tyr Ser Ser Val Leu Thr Gly Ala Val Leu Phe Ser Ser
                        325                      330                      335

Thr Ile Ile Ser Ile Ser Thr Val Asp Arg Leu Gly Arg Arg Lys Leu
                340                      345                      350

Leu Ile Ser Gly Gly Ile Gln Met Ile Ile Cys Gln Val Ile Val Ala
                355                      360                      365

Val Ile Leu Gly Val Lys Phe Gly Thr Asp Lys Glu Leu Thr Arg Ser
                370                      375                      380

Tyr Ser Ile Ala Val Val Val Ile Cys Leu Phe Val Leu Ala Phe
385                      390                      395                      400

Gly Trp Ser Trp Gly Pro Leu Gly Trp Thr Val Pro Ser Glu Ile Phe
                        405                      410                      415

Pro Leu Glu Thr Arg Ser Ala Gly Gln Ser Ile Thr Val Ala Val Asn
                        420                      425                      430

Leu Phe Phe Thr Phe Val Ile Ala Gln Ala Phe Leu Ser Leu Leu Cys
                        435                      440                      445

Ala Leu Lys Phe Gly Ile Phe Leu Phe Phe Ala Gly Trp Ile Thr Val
                450                      455                      460

Met Thr Val Phe Val His Val Phe Leu Pro Glu Thr Lys Gly Val Pro
465                      470                      475                      480
```

-continued

```
Ile Glu Glu Met Val Leu Leu Trp Arg Lys His Trp Phe Trp Lys Lys
                485                 490                 495
Val Met Pro Asp Leu Pro Leu Glu Asp Gly Asp Ser His His Lys
            500                 505                 510

<210> SEQ ID NO 13
<211> LENGTH: 490
<212> TYPE: DNA
<213> ORGANISM: Sorghum

<400> SEQUENCE: 13
gcacgaggcc cagcgagctg ttcccgctgg agatgcggtc ggcggggcag agcgtggtgg      60
tgtgcgtcaa cctcttctgg acggccgccg tggcgcagtg cttcctggcg gcgctgtgcc     120
acctccggtg gggcgtcttc gtgctcttcg cctcgctcat cgtcgtcatg tccatcttcg     180
tcatcctcct gctgccggag acgaagcagg tgcccatcga ggagatctgg atgctcttcg     240
acaagcactg gtactggaag cgcatcgtcc gcagggaccc aaagtaccag ggcaacctcc     300
accagcagca gcagcagcag cagcagcagg agatgtccaa agcatgaaca tgattaacaa     360
tgtgatttaa taagttctct actccaaatc tatatgagat gattactcct agatgaatgt     420
ggtgtgattc ttgatgcaat ccaaaagagg atgagttagg attggtgttg caaaaaaaaa     480
aaaaaaaaaa                                                           490

<210> SEQ ID NO 14
<211> LENGTH: 114
<212> TYPE: PRT
<213> ORGANISM: Sorghum

<400> SEQUENCE: 14

Thr Arg Pro Ser Glu Leu Phe Pro Leu Glu Met Arg Ser Ala Gly Gln
  1               5                  10                  15
Ser Val Val Val Cys Val Asn Leu Phe Trp Thr Ala Ala Val Ala Gln
                 20                  25                  30
Cys Phe Leu Ala Ala Leu Cys His Leu Arg Trp Gly Val Phe Val Leu
             35                  40                  45
Phe Ala Ser Leu Ile Val Val Met Ser Ile Phe Val Ile Leu Leu Leu
         50                  55                  60
Pro Glu Thr Lys Gln Val Pro Ile Glu Glu Ile Trp Met Leu Phe Asp
 65                  70                  75                  80
Lys His Trp Tyr Trp Lys Arg Ile Val Arg Arg Asp Pro Lys Tyr Gln
                 85                  90                  95
Gly Asn Leu His Gln Gln Gln Gln Gln Gln Gln Gln Glu Met Ser
                100                 105                 110
Lys Ala

<210> SEQ ID NO 15
<211> LENGTH: 1960
<212> TYPE: DNA
<213> ORGANISM: Glycine max
<220> FEATURE:
<221> NAME/KEY: unsure
<222> LOCATION: (10)
<223> OTHER INFORMATION: n = a, c, g or t
<220> FEATURE:
<221> NAME/KEY: unsure
<222> LOCATION: (28)
<223> OTHER INFORMATION: n = a, c, g or t
<220> FEATURE:
<221> NAME/KEY: unsure
```

```
<222> LOCATION: (514)
<223> OTHER INFORMATION: n = a, c, g or t
<220> FEATURE:
<221> NAME/KEY: unsure
<222> LOCATION: (533)
<223> OTHER INFORMATION: n = a, c, g or t
<220> FEATURE:
<221> NAME/KEY: unsure
<222> LOCATION: (542)
<223> OTHER INFORMATION: n = a, c, g or t
<220> FEATURE:
<221> NAME/KEY: unsure
<222> LOCATION: (552)
<223> OTHER INFORMATION: n = a, c, g or t
<220> FEATURE:
<221> NAME/KEY: unsure
<222> LOCATION: (620)
<223> OTHER INFORMATION: n = a, c, g or t

<400> SEQUENCE: 15
attcaacgan aatctgggct atataaanac ttgcccctcc ccatccaaaa gctccatctt      60
gtttctcttt cttgtatctt ctcaccccag tttcactttc tcattatttt ctctcctatt     120
gataaagaaa cagagagaga gagaaaaaaa tgcctgcggt aggaggtatt agcaacggag     180
ggggcaagga gtaccctgga agcctcactc cttttgtgac ggtaacatgt atagttgcag     240
ccatgggtgg gttaatcttc ggttacgata tcggaatttc aggtgggtg acatccatgg      300
atccgtttct gctcaagttt ttcccgtcgg tgttccggaa gaagaattcc gacaaaacgg     360
tgaaccagta ctgtcaatac gacagtcaga cactgacgat gttcacgtcg tcgctgtatc     420
tcgccgcgtt gctgtcgtcg ttggttgcct ccaccgtcac acgtaggttc ggccgraaam     480
tctccatgct tttcggaggc ttgcttttcc tcgncggtgc ccttatcaac ggnttttgccc    540
ancacgtgtg gntgctcatc gtgggtcgga tcttgctcgg gttcggtatc cggtttgcca     600
atcagtctgt gccactctan ctatctgaaa tggctccata caaatataga ggagcattga     660
acattggctt tcagttgtcc atcactgttg gtatccttgt ggccaatgtg ttgaactatt     720
tctttgctaa atcaaaggt ggttggggat ggaggttgag tttgggaggt gctatggtcc      780
ctgcccttat aatcacagta ggatcactag tccttccaga cactcccaat tccatgattg     840
aaagggtgga tcgcgagaag gccaaggctc agcttcagag aattcgcggc atcgacaatg     900
ttgatgaaga gttcaatgac cttgtggcag caagtgaatc ctctagccaa gtggagcacc     960
cttggaggaa cttgttgcaa agaaagtaca gaccccacct caccatggca gtgttgattc    1020
cattcttcca gcaactcact ggaatcaatg tcatcatgtt ttacgcgccg gtcctgttca    1080
gctccatcgg gtttaaggat gatgctgctc taatgtcagc tgtgatcacc ggcgttgtta    1140
atgttgtcgc aacttgtgtc tcaatttatg gtgttgacaa gtggggtagg agagcccttt    1200
tccttgaagg tggagtccaa atgctcattt gccaggctgt agttgcagct gcaattggag    1260
caaagtttgg aactgatggg aacccaggtg atttgccaaa gtggtatgca attgttgtgg    1320
ttctcttcat ttgcattat gtatcagcat ttgcctggtc atgggtccc ctaggttggt      1380
tggtgcctag tgagatcttt cccttggaga ttcgttcagc tgctcagagt atcaatgtgt    1440
cggtgaacat gcttttcact ttcttgattg cacaagtctt cttgacaatg ctttgccaca    1500
tgaagttcgg cttgttcctc ttctttgcct tcttcgtgtt gatcatgaca ttcttcgtct    1560
acttcttctt gcccgaaaca aagggcattc caattgaaga atggggcag gtttggcagg     1620
cacaccccct ctggtccaga ttcgtggagc atgatgatta tggcaatggt gttgagatgg    1680
gaaagggagc tattaaagaa gtgtagttag tcctcgtctt ggtttatttt tctcaatgac    1740
```

```
tagcgtttta gcttttgttg gtaaatcata ctattggttt caatgtattg aattgttcct    1800
aaaaattaaa aagggttatt tttcttatgt atcccctgct tcttcatatg aagcaagttt    1860
acaggatact tttctatatt aatccaattg cacaaattgt tatgcctttg aaacaaaaa     1920 aaaaaaaaaa aaaaaaaaaa aaaaaaaaaa aaaaaaaaa                            1960
```

<210> SEQ ID NO 16
<211> LENGTH: 518
<212> TYPE: PRT
<213> ORGANISM: Glycine max
<220> FEATURE:
<221> NAME/KEY: UNSURE
<222> LOCATION: (111)
<223> OTHER INFORMATION: Xaa = any amino acid
<220> FEATURE:
<221> NAME/KEY: UNSURE
<222> LOCATION: (122)
<223> OTHER INFORMATION: Xaa = any amino acid
<220> FEATURE:
<221> NAME/KEY: UNSURE
<222> LOCATION: (131)
<223> OTHER INFORMATION: Xaa = any amino acid
<220> FEATURE:
<221> NAME/KEY: UNSURE
<222> LOCATION: (135)
<223> OTHER INFORMATION: Xaa = any amino acid
<220> FEATURE:
<221> NAME/KEY: UNSURE
<222> LOCATION: (157)
<223> OTHER INFORMATION: Xaa = any amino acid

<400> SEQUENCE: 16

```
Met Pro Ala Val Gly Gly Ile Ser Asn Gly Gly Gly Lys Glu Tyr Pro
  1               5                  10                  15

Gly Ser Leu Thr Pro Phe Val Thr Val Thr Cys Ile Val Ala Ala Met
             20                  25                  30

Gly Gly Leu Ile Phe Gly Tyr Asp Ile Gly Ile Ser Gly Gly Val Thr
         35                  40                  45

Ser Met Asp Pro Phe Leu Leu Lys Phe Phe Pro Ser Val Phe Arg Lys
     50                  55                  60

Lys Asn Ser Asp Lys Thr Val Asn Gln Tyr Cys Gln Tyr Asp Ser Gln
 65                  70                  75                  80

Thr Leu Thr Met Phe Thr Ser Ser Leu Tyr Leu Ala Ala Leu Leu Ser
                 85                  90                  95

Ser Leu Val Ala Ser Thr Val Thr Arg Arg Phe Gly Arg Lys Xaa Ser
            100                 105                 110

Met Leu Phe Gly Gly Leu Leu Phe Leu Xaa Gly Ala Leu Ile Asn Gly
        115                 120                 125

Phe Ala Xaa His Val Trp Xaa Leu Ile Val Gly Arg Ile Leu Leu Gly
    130                 135                 140

Phe Gly Ile Arg Phe Ala Asn Gln Ser Val Pro Leu Xaa Leu Ser Glu
145                 150                 155                 160

Met Ala Pro Tyr Lys Tyr Arg Gly Ala Leu Asn Ile Gly Phe Gln Leu
                165                 170                 175

Ser Ile Thr Val Gly Ile Leu Val Ala Asn Val Leu Asn Tyr Phe Phe
            180                 185                 190

Ala Lys Ile Lys Gly Gly Trp Gly Trp Arg Leu Ser Leu Gly Gly Ala
        195                 200                 205

Met Val Pro Ala Leu Ile Ile Thr Val Gly Ser Leu Val Leu Pro Asp
    210                 215                 220

Thr Pro Asn Ser Met Ile Glu Arg Gly Asp Arg Glu Lys Ala Lys Ala
```

```
                225                 230                 235                 240
Gln Leu Gln Arg Ile Arg Gly Ile Asp Asn Val Asp Glu Phe Asn
                245                 250                 255
Asp Leu Val Ala Ala Ser Glu Ser Ser Gln Val Glu His Pro Trp
            260                 265                 270
Arg Asn Leu Leu Gln Arg Lys Tyr Arg Pro His Leu Thr Met Ala Val
        275                 280                 285
Leu Ile Pro Phe Phe Gln Gln Leu Thr Gly Ile Asn Val Ile Met Phe
    290                 295                 300
Tyr Ala Pro Val Leu Phe Ser Ser Ile Gly Phe Lys Asp Asp Ala Ala
305                 310                 315                 320
Leu Met Ser Ala Val Ile Thr Gly Val Val Asn Val Val Ala Thr Cys
                325                 330                 335
Val Ser Ile Tyr Gly Val Asp Lys Trp Gly Arg Arg Ala Leu Phe Leu
                340                 345                 350
Glu Gly Gly Val Gln Met Leu Ile Cys Gln Ala Val Val Ala Ala Ala
                355                 360                 365
Ile Gly Ala Lys Phe Gly Thr Asp Gly Asn Pro Gly Asp Leu Pro Lys
    370                 375                 380
Trp Tyr Ala Ile Val Val Leu Phe Ile Cys Ile Tyr Val Ser Ala
385                 390                 395                 400
Phe Ala Trp Ser Trp Gly Pro Leu Gly Trp Leu Val Pro Ser Glu Ile
                405                 410                 415
Phe Pro Leu Glu Ile Arg Ser Ala Ala Gln Ser Ile Asn Val Ser Val
                420                 425                 430
Asn Met Leu Phe Thr Phe Leu Ile Ala Gln Val Phe Leu Thr Met Leu
                435                 440                 445
Cys His Met Lys Phe Gly Leu Phe Leu Phe Phe Ala Phe Phe Val Leu
    450                 455                 460
Ile Met Thr Phe Phe Val Tyr Phe Phe Leu Pro Glu Thr Lys Gly Ile
465                 470                 475                 480
Pro Ile Glu Glu Met Gly Gln Val Trp Gln Ala His Pro Phe Trp Ser
                485                 490                 495
Arg Phe Val Glu His Asp Asp Tyr Gly Asn Gly Val Glu Met Gly Lys
                500                 505                 510
Gly Ala Ile Lys Glu Val
            515

<210> SEQ ID NO 17
<211> LENGTH: 1752
<212> TYPE: DNA
<213> ORGANISM: Triticum aestivum

<400> SEQUENCE: 17
ttcatcatca gctttgagcc agcttaatca ttctagtgct ctgagttctt accgaccgac      60
caaccatggc gggcggcgcc gtcgtgaaca cgtccggcgg caaggactac cctggcaggc     120
tcaccctctt cgtcttcttc acctgcgtcg tcgccgccac cggcggcctc atctttggat     180
atgacatcgg tatctcaggg ggcgttacgt ccatgaaccc tttcctgaaa aagttcttcc     240
cggaggtgta tgacaagaag cagatgaagg gctccgccac ccagtactgc aagtacgaca     300
accagctgct ccagaccttc acctcctccc tctacctcgc ggcgctcgtc tcctccttct     360
tcgccgccac cgtcacacgt gtcgtgggcc gtaagtggtc catgttcacc ggagggctca     420
ccttcctcat cggcgctgcg cttaacgggg cggcggagaa catcgccatg ctcatcgtcg     480
```

-continued

```
gacgcatcct cctcggtgtc ggcgttggct tcgccaatca gtctgtgccg gtgtacctgt    540
cggagatggc gcctgcgcgt ctccggggca tgctcaacat cgggttccag ctcatgatca    600
ccatcggcat cctggcggcg gcgctcatca attacgacac caacaagatc aaggccgggt    660
acgggtggcg catcagcctg ccatcgcgcg ccgtcccggc gggcatcatc accctgggg t    720
ccttttcct ccccgacacc cccaactccc tcatcgagcg tggccaccg gaggcggcgc      780
gccgcatgct caaccgcatc cgcggcagcg acgtggacat cagcgaggag tacgcggacc    840
tggtggtggc gagcgaggag tccaagctgg tgcagcaccc gtggcgcaac atcctgcagc    900
gcaagtaccg gccccagctg accatggcga tcatgatccc cttcttccag cagctgacgg    960
gcatcaacgt catcatgttc tacgcgccgg tgctgttcga gacgctgggg ttcaagggcg   1020
acgcgtcgct catgtcggcc gtcatcacgg gcctggtcaa cgtgttcgcg acgctcgtgt   1080
ccgtgttcac cgtcgaccgg ctgggtcgcc ggaagctgtt cctgcagggc ggcacgcaga   1140
tgctgctgag ccagctggtg gtgggcaccc tgatcgcggt caagttcggg acgagcggcg   1200
tgggggagat gccaagggg tacgcggcgg cggtggtgct cttcatctgc ctctatgtgg    1260
ccgggttcgc gtggtcgtgg gggcccctgg ggtggctggt gcccagcgag atcttcccgc   1320
tggagatcag gccggcgggg cagagcatca acgtgtcggt gaacatgctc ttcaccttcg   1380
tcatcgcgca ggcgttcctc accatgctct gccacatgaa gttcggcctc ttctacttct   1440
tcgccggctg ggtggtgatc atgaccgtct tcatcgcgct cttcctgccg gagaccaaga   1500
acgtgcccat cgaggagatg gtgctcgtct ggaagggaca ctggttctgg cgcaggtaca   1560
tcggagacgc tgacgtccac gtcggcgcca acaacggcaa gggcgccgcc atcgcataga   1620
ttccttcctt tcctagctcc gtctccctcg tgtacattaa ttgcttttct tcctctcttc   1680
cttgtttgtc ctcgtagatg catgcttagg tcaaaccgtg tgtttctctt ctgtaaaaaa   1740
aaaaaaaaaa aa                                                       1752
```

<210> SEQ ID NO 18
<211> LENGTH: 517
<212> TYPE: PRT
<213> ORGANISM: Triticum aestivum

<400> SEQUENCE: 18

```
Met Ala Gly Gly Ala Val Val Asn Thr Ser Gly Gly Lys Asp Tyr Pro
 1               5                  10                  15

Gly Arg Leu Thr Leu Phe Val Phe Phe Thr Cys Val Val Ala Ala Thr
            20                  25                  30

Gly Gly Leu Ile Phe Gly Tyr Asp Ile Gly Ile Ser Gly Gly Val Thr
        35                  40                  45

Ser Met Asn Pro Phe Leu Lys Lys Phe Phe Pro Glu Val Tyr Asp Lys
    50                  55                  60

Lys Gln Met Lys Gly Ser Ala Ser Gln Tyr Cys Lys Tyr Asp Asn Gln
65                  70                  75                  80

Leu Leu Gln Thr Phe Thr Ser Ser Leu Tyr Leu Ala Ala Leu Val Ser
                85                  90                  95

Ser Phe Phe Ala Ala Thr Val Thr Arg Val Val Gly Arg Lys Trp Ser
            100                 105                 110

Met Phe Thr Gly Gly Leu Thr Phe Leu Ile Gly Ala Ala Leu Asn Gly
        115                 120                 125

Ala Ala Glu Asn Ile Ala Met Leu Ile Val Gly Arg Ile Leu Leu Gly
    130                 135                 140
```

Val Gly Val Gly Phe Ala Asn Gln Ser Val Pro Val Tyr Leu Ser Glu
145                 150                 155                 160

Met Ala Pro Ala Arg Leu Arg Gly Met Leu Asn Ile Gly Phe Gln Leu
            165                 170                 175

Met Ile Thr Ile Gly Ile Leu Ala Ala Ala Leu Ile Asn Tyr Asp Thr
            180                 185                 190

Asn Lys Ile Lys Ala Gly Tyr Gly Trp Arg Ile Ser Leu Ala Ile Ala
            195                 200                 205

Ala Val Pro Ala Gly Ile Ile Thr Leu Gly Ser Phe Phe Leu Pro Asp
210                 215                 220

Thr Pro Asn Ser Leu Ile Glu Arg Gly His Pro Glu Ala Ala Arg Arg
225                 230                 235                 240

Met Leu Asn Arg Ile Arg Gly Ser Asp Val Asp Ile Ser Glu Glu Tyr
            245                 250                 255

Ala Asp Leu Val Val Ala Ser Glu Glu Ser Lys Leu Val Gln His Pro
            260                 265                 270

Trp Arg Asn Ile Leu Gln Arg Lys Tyr Arg Pro Gln Leu Thr Met Ala
            275                 280                 285

Ile Met Ile Pro Phe Phe Gln Gln Leu Thr Gly Ile Asn Val Ile Met
290                 295                 300

Phe Tyr Ala Pro Val Leu Phe Glu Thr Leu Gly Phe Lys Gly Asp Ala
305                 310                 315                 320

Ser Leu Met Ser Ala Val Ile Thr Gly Leu Val Asn Val Phe Ala Thr
            325                 330                 335

Leu Val Ser Val Phe Thr Val Asp Arg Leu Gly Arg Arg Lys Leu Phe
            340                 345                 350

Leu Gln Gly Gly Thr Gln Met Leu Leu Ser Gln Leu Val Val Gly Thr
            355                 360                 365

Leu Ile Ala Val Lys Phe Gly Thr Ser Gly Val Gly Glu Met Pro Lys
370                 375                 380

Gly Tyr Ala Ala Ala Val Val Leu Phe Ile Cys Leu Tyr Val Ala Gly
385                 390                 395                 400

Phe Ala Trp Ser Trp Gly Pro Leu Gly Trp Leu Val Pro Ser Glu Ile
            405                 410                 415

Phe Pro Leu Glu Ile Arg Pro Ala Gly Gln Ser Ile Asn Val Ser Val
            420                 425                 430

Asn Met Leu Phe Thr Phe Val Ile Ala Gln Ala Phe Leu Thr Met Leu
            435                 440                 445

Cys His Met Lys Phe Gly Leu Phe Tyr Phe Ala Gly Trp Val Val
450                 455                 460

Ile Met Thr Val Phe Ile Ala Leu Phe Leu Pro Glu Thr Lys Asn Val
465                 470                 475                 480

Pro Ile Glu Glu Met Val Leu Val Trp Lys Gly His Trp Phe Trp Arg
            485                 490                 495

Arg Tyr Ile Gly Asp Ala Asp Val His Val Gly Ala Asn Asn Gly Lys
            500                 505                 510

Gly Ala Ala Ile Ala
        515

<210> SEQ ID NO 19
<211> LENGTH: 510
<212> TYPE: PRT
<213> ORGANISM: Ricinus communis
<220> FEATURE:

<221> NAME/KEY: UNSURE
<222> LOCATION: (117)
<223> OTHER INFORMATION: Xaa = any amino acid
<220> FEATURE:
<221> NAME/KEY: UNSURE
<222> LOCATION: (122)
<223> OTHER INFORMATION: Xaa = any amino acid

<400> SEQUENCE: 19

```
Met Ala Gly Leu Ala Ile Thr Ser Glu Gly Gly Gln Tyr Asn Gly
 1               5                  10                  15

Arg Met Thr Ser Phe Val Ala Leu Ser Cys Met Met Ala Ala Met Gly
             20                  25                  30

Gly Val Ile Phe Gly Tyr Asp Ile Gly Val Ser Gly Val Thr Ser
             35                  40                  45

Met Asp Pro Phe Leu Lys Lys Phe Phe Pro Asp Val Tyr Arg Lys Met
 50                  55                  60

Lys Glu Asp Thr Glu Ile Ser Asn Tyr Cys Lys Phe Asp Ser Gln Leu
 65                  70                  75                  80

Leu Thr Ser Phe Thr Ser Ser Leu Tyr Val Ala Gly Leu Val Ala Ser
                 85                  90                  95

Phe Phe Ala Ser Ser Val Thr Arg Ala Phe Gly Arg Lys Pro Ser Ile
                100                 105                 110

Leu Leu Gly Gly Xaa Val Phe Leu Ala Xaa Ala Ala Leu Gly Gly Ala
            115                 120                 125

Ala Val Asn Val Tyr Met Leu Ile Phe Gly Arg Val Leu Leu Gly Val
        130                 135                 140

Gly Val Gly Phe Ala Asn Gln Ala Val Pro Leu Tyr Leu Ser Glu Met
145                 150                 155                 160

Ala Pro Pro Arg Tyr Arg Gly Ala Ile Asn Asn Gly Phe Gln Phe Ser
                165                 170                 175

Val Gly Ile Gly Ala Leu Ser Ala Asn Leu Ile Asn Tyr Gly Thr Glu
            180                 185                 190

Lys Ile Glu Gly Gly Trp Gly Trp Arg Ile Ser Leu Ala Met Ala Ala
        195                 200                 205

Val Pro Ala Ala Ile Leu Thr Phe Gly Ala Leu Phe Leu Pro Glu Thr
    210                 215                 220

Pro Asn Ser Leu Ile Gln Arg Ser Asn Asp His Glu Arg Ala Lys Leu
225                 230                 235                 240

Met Leu Gln Arg Val Arg Gly Thr Thr Asp Val Gln Ala Glu Leu Asp
                245                 250                 255

Asp Leu Ile Lys Ala Ser Ile Ile Ser Arg Thr Ile Gln His Pro Phe
            260                 265                 270

Lys Asn Ile Met Arg Arg Lys Tyr Arg Pro Gln Leu Val Met Ala Val
        275                 280                 285

Ala Ile Pro Phe Phe Gln Gln Val Thr Gly Ile Asn Val Ile Ala Phe
    290                 295                 300

Tyr Ala Pro Ile Leu Phe Arg Thr Ile Gly Leu Glu Glu Ser Ala Ser
305                 310                 315                 320

Leu Leu Ser Ser Ile Val Thr Gly Leu Val Gly Ser Ala Ser Thr Phe
                325                 330                 335

Ile Ser Met Leu Ile Val Asp Lys Leu Gly Arg Arg Ala Leu Phe Ile
            340                 345                 350

Phe Gly Gly Val Gln Met Phe Val Ala Gln Ile Met Val Gly Ser Ile
        355                 360                 365
```

```
Met Ala Ala Glu Leu Gly Asp His Gly Gly Ile Gly Lys Gly Tyr Ala
    370                 375                 380

Tyr Ile Val Leu Ile Leu Ile Cys Ile Tyr Val Ala Gly Phe Gly Trp
385                 390                 395                 400

Ser Trp Gly Pro Leu Gly Trp Leu Val Pro Ser Glu Ile Phe Pro Leu
                405                 410                 415

Glu Ile Arg Ser Ala Gly Gln Ser Ile Val Val Ala Val Ser Phe Leu
            420                 425                 430

Phe Thr Phe Val Val Ala Gln Thr Phe Leu Ser Met Leu Cys His Phe
        435                 440                 445

Lys Ser Gly Ile Phe Phe Phe Gly Gly Trp Val Val Met Thr
    450                 455                 460

Ala Phe Val His Phe Leu Leu Pro Glu Thr Lys Lys Val Pro Ile Glu
465                 470                 475                 480

Lys Met Asp Ile Val Trp Arg Asp His Trp Phe Trp Lys Lys Ile Ile
                485                 490                 495

Gly Glu Glu Ala Ala Glu Glu Asn Asn Lys Met Glu Ala Ala
                500                 505                 510

<210> SEQ ID NO 20
<211> LENGTH: 287
<212> TYPE: PRT
<213> ORGANISM: Saccharum sp.

<400> SEQUENCE: 20

Ile Glu Arg Gly Arg Val Glu Gly Arg Arg Val Leu Glu Arg Ile
  1               5                  10                  15

Arg Gly Thr Ala Asp Val Asp Ala Glu Phe Thr Asp Met Val Glu Ala
                20                  25                  30

Ser Glu Leu Ala Asn Thr Ile Glu His Pro Phe Arg Asn Ile Leu Glu
            35                  40                  45

Pro Arg Asn Arg Pro Gln Leu Val Met Ala Val Cys Met Pro Ala Phe
        50                  55                  60

Gln Ile Leu Thr Gly Ile Asn Ser Ile Leu Phe Tyr Ala Pro Val Leu
 65                 70                  75                  80

Phe Gln Ser Met Gly Phe Gly Asn Ala Ser Leu Tyr Ser Ser Val
                85                  90                  95

Leu Thr Gly Ala Val Leu Phe Ser Ser Thr Leu Ile Ser Ile Gly Thr
            100                 105                 110

Val Asp Arg Leu Gly Arg Arg Lys Leu Leu Ile Ser Gly Gly Ile Gln
        115                 120                 125

Met Ile Val Cys Gln Val Ile Val Ala Val Ile Leu Gly Ala Lys Phe
    130                 135                 140

Gly Ala Asp Lys Gln Leu Ser Arg Ser Tyr Ser Ile Ala Val Val Val
145                 150                 155                 160

Val Ile Cys Leu Phe Val Leu Ala Phe Gly Trp Ser Trp Gly Pro Leu
                165                 170                 175

Gly Trp Thr Val Pro Ser Glu Ile Phe Pro Leu Glu Thr Arg Ser Ala
            180                 185                 190

Gly Gln Ser Ile Thr Val Ala Val Asn Leu Leu Phe Thr Phe Ala Ile
        195                 200                 205

Ala Gln Ala Phe Leu Ser Leu Leu Cys Ala Phe Lys Phe Gly Ile Phe
    210                 215                 220

Leu Phe Phe Ala Gly Trp Ile Thr Val Met Thr Val Phe Val Cys Val
225                 230                 235                 240
```

-continued

Phe Leu Pro Glu Thr Lys Gly Val Pro Ile Glu Met Val Leu Leu
                245                 250                 255

Trp Arg Lys His Trp Phe Trp Lys Lys Val Met Pro Ala Asp Met Pro
            260                 265                 270

Leu Glu Asp Gly Trp Gly Ala Ala Pro Ala Ser Asn Asn His Lys
        275                 280                 285

<210> SEQ ID NO 21
<211> LENGTH: 504
<212> TYPE: PRT
<213> ORGANISM: Arabidopsis thaliana

<400> SEQUENCE: 21

Met Ala Gly Gly Ala Leu Thr Asp Glu Gly Leu Lys Arg Ala His
 1               5                  10                  15

Leu Tyr Glu His Arg Ile Thr Ser Tyr Phe Ile Phe Ala Cys Ile Val
            20                  25                  30

Gly Ser Met Gly Gly Ser Leu Phe Gly Tyr Asp Leu Gly Val Ser Gly
        35                  40                  45

Gly Val Thr Ser Met Asp Asp Phe Leu Lys Glu Phe Phe Pro Gly Ile
    50                  55                  60

Tyr Lys Arg Lys Gln Met His Leu Asn Glu Thr Asp Tyr Cys Lys Tyr
65                  70                  75                  80

Asp Asn Gln Ile Leu Thr Leu Phe Thr Ser Ser Leu Tyr Phe Ala Gly
                85                  90                  95

Leu Ile Ser Thr Phe Gly Ala Ser Tyr Val Thr Arg Ile Tyr Gly Arg
            100                 105                 110

Arg Gly Ser Ile Leu Val Gly Ser Val Ser Phe Phe Leu Gly Gly Val
        115                 120                 125

Ile Asn Ala Ala Ala Lys Asn Ile Leu Met Leu Ile Leu Gly Arg Ile
    130                 135                 140

Phe Leu Gly Ile Gly Ile Gly Phe Gly Asn Gln Ala Val Pro Leu Tyr
145                 150                 155                 160

Leu Ser Glu Met Ala Pro Ala Lys Ile Arg Gly Thr Val Asn Gln Leu
                165                 170                 175

Phe Gln Leu Thr Thr Cys Ile Gly Ile Leu Val Ala Asn Leu Ile Asn
            180                 185                 190

Tyr Lys Thr Glu Gln Ile His Pro Trp Gly Trp Arg Leu Ser Leu Gly
        195                 200                 205

Leu Ala Thr Val Pro Ala Ile Leu Met Phe Leu Gly Gly Leu Val Leu
    210                 215                 220

Pro Glu Thr Pro Asn Ser Leu Val Glu Gln Gly Lys Leu Glu Lys Ala
225                 230                 235                 240

Lys Ala Val Leu Ile Lys Val Arg Gly Thr Asn Asn Ile Glu Ala Glu
                245                 250                 255

Phe Gln Asp Leu Val Glu Ala Ser Asp Ala Ala Arg Ala Val Lys Asn
            260                 265                 270

Pro Phe Arg Asn Leu Leu Ala Arg Arg Asn Arg Pro Gln Leu Val Ile
        275                 280                 285

Gly Ala Ile Gly Leu Pro Ala Phe Gln Gln Leu Thr Gly Met Asn Ser
    290                 295                 300

Ile Leu Phe Tyr Ala Pro Val Met Phe Gln Ser Leu Gly Phe Gly Gly
305                 310                 315                 320

Ser Ala Ser Leu Ile Ser Ser Thr Ile Thr Asn Ala Ala Leu Val Val

```
                        325                 330                 335
Ala Ala Ile Met Ser Met Tyr Ser Ala Asp Lys Phe Gly Arg Arg Phe
                340                 345                 350
Leu Leu Leu Glu Ala Ser Val Glu Met Phe Cys Tyr Met Val Val Val
                355                 360                 365
Gly Val Thr Leu Ala Leu Lys Phe Gly Glu Gly Lys Glu Leu Pro Lys
                370                 375                 380
Ser Leu Gly Leu Ile Leu Val Val Leu Ile Cys Leu Phe Val Leu Ala
385                 390                 395                 400
Tyr Gly Arg Ser Trp Gly Pro Met Gly Trp Leu Val Pro Ser Glu Leu
                405                 410                 415
Phe Pro Leu Glu Thr Arg Ser Ala Gly Gln Ser Val Val Cys Val
                420                 425                 430
Asn Leu Phe Phe Thr Ala Leu Ile Ala Gln Cys Phe Leu Val Ser Leu
                435                 440                 445
Cys His Leu Lys Tyr Gly Ile Phe Leu Leu Phe Ala Gly Leu Ile Leu
                450                 455                 460
Gly Met Gly Ser Phe Val Tyr Phe Leu Leu Pro Glu Thr Lys Gln Val
465                 470                 475                 480
Pro Ile Glu Glu Val Tyr Leu Leu Trp Arg Gln His Trp Leu Trp Lys
                485                 490                 495
Lys Tyr Val Glu Asp Val Asp Glu
                500

<210> SEQ ID NO 22
<211> LENGTH: 514
<212> TYPE: PRT
<213> ORGANISM: Arabidopsis thaliana

<400> SEQUENCE: 22

Met Ala Gly Gly Phe Val Ser Gln Thr Pro Gly Val Arg Asn Tyr Asn
  1               5                  10                  15
Tyr Lys Leu Thr Pro Lys Val Phe Val Thr Cys Phe Ile Gly Ala Phe
                 20                  25                  30
Gly Gly Leu Ile Phe Gly Tyr Asp Leu Gly Ile Ser Gly Gly Val Thr
                 35                  40                  45
Ser Met Glu Pro Phe Leu Glu Glu Phe Phe Pro Tyr Val Tyr Lys Lys
         50                  55                  60
Met Lys Ser Ala His Glu Asn Glu Tyr Cys Arg Phe Asp Ser Gln Leu
 65                  70                  75                  80
Leu Thr Leu Phe Thr Ser Ser Leu Tyr Val Ala Ala Leu Val Ser Ser
                 85                  90                  95
Leu Phe Ala Ser Thr Ile Thr Arg Val Phe Gly Arg Lys Trp Ser Met
                100                 105                 110
Phe Leu Gly Gly Phe Thr Phe Phe Ile Gly Ser Ala Phe Asn Gly Phe
            115                 120                 125
Ala Gln Asn Ile Ala Met Leu Leu Ile Gly Arg Ile Leu Leu Gly Phe
        130                 135                 140
Gly Val Gly Phe Ala Asn Gln Ser Val Pro Val Tyr Leu Ser Glu Met
145                 150                 155                 160
Ala Pro Pro Asn Leu Arg Gly Ala Phe Asn Asn Gly Phe Gln Val Ala
                165                 170                 175
Ile Ile Phe Gly Ile Val Val Ala Thr Ile Ile Asn Tyr Phe Thr Ala
                180                 185                 190
```

-continued

```
Gln Met Lys Gly Asn Ile Gly Trp Arg Ile Ser Leu Gly Leu Ala Cys
        195                 200                 205

Val Pro Ala Val Met Ile Met Ile Gly Ala Leu Ile Leu Pro Asp Thr
    210                 215                 220

Pro Asn Ser Leu Ile Glu Arg Gly Tyr Thr Glu Ala Lys Glu Met
225                 230                 235                 240

Leu Gln Ser Ile Arg Gly Thr Asn Glu Val Asp Glu Phe Gln Asp
                245                 250                 255

Leu Ile Asp Ala Ser Glu Glu Ser Lys Gln Val Lys His Pro Trp Lys
                260                 265                 270

Asn Ile Met Leu Pro Arg Tyr Arg Pro Gln Leu Ile Met Thr Cys Phe
                275                 280                 285

Ile Pro Phe Phe Gln Gln Leu Thr Gly Ile Asn Val Ile Thr Phe Tyr
        290                 295                 300

Ala Pro Val Leu Phe Gln Thr Leu Gly Phe Gly Ser Lys Ala Ser Leu
305                 310                 315                 320

Leu Ser Ala Met Val Thr Gly Ile Ile Glu Leu Leu Cys Thr Phe Val
                325                 330                 335

Ser Val Phe Thr Val Asp Arg Phe Gly Arg Arg Ile Leu Phe Leu Gln
                340                 345                 350

Gly Gly Ile Gln Met Leu Val Ser Gln Ile Ala Ile Gly Ala Met Ile
                355                 360                 365

Gly Val Lys Phe Gly Val Ala Gly Thr Gly Asn Ile Gly Lys Ser Asp
        370                 375                 380

Ala Asn Leu Ile Val Ala Leu Ile Cys Ile Tyr Val Ala Gly Phe Ala
385                 390                 395                 400

Trp Ser Trp Gly Pro Leu Gly Trp Leu Val Pro Ser Glu Ile Ser Pro
                405                 410                 415

Leu Glu Ile Arg Ser Ala Ala Gln Ala Ile Asn Val Ser Val Asn Met
                420                 425                 430

Phe Phe Thr Phe Leu Val Ala Gln Leu Phe Leu Thr Met Leu Cys His
        435                 440                 445

Met Lys Phe Gly Leu Phe Phe Phe Ala Phe Phe Val Val Ile Met
    450                 455                 460

Thr Ile Phe Ile Tyr Leu Met Leu Pro Glu Thr Lys Asn Val Pro Ile
465                 470                 475                 480

Glu Glu Met Asn Arg Val Trp Lys Ala His Trp Phe Trp Gly Lys Phe
                485                 490                 495

Ile Pro Asp Glu Ala Val Asn Met Gly Ala Ala Glu Met Gln Gln Lys
                500                 505                 510

Ser Val
```

```
<210> SEQ ID NO 23
<211> LENGTH: 518
<212> TYPE: PRT
<213> ORGANISM: Medicago truncatula

<400> SEQUENCE: 23
```

```
Met Ala Gly Gly Gly Ile Pro Ile Gly Gly Asn Lys Glu Tyr Pro
1               5                  10                  15

Gly Asn Leu Thr Pro Phe Val Thr Ile Thr Cys Ile Val Ala Ala Met
                20                  25                  30

Gly Gly Leu Ile Phe Gly Tyr Asp Ile Gly Ile Ser Gly Gly Val Thr
            35                  40                  45
```

-continued

```
Ser Met Asp Pro Phe Leu Lys Lys Phe Phe Pro Ala Val Tyr Arg Lys
     50                  55                  60

Lys Asn Lys Asp Lys Ser Thr Asn Gln Tyr Cys Gln Tyr Asp Ser Gln
 65                  70                  75                  80

Thr Leu Thr Met Phe Thr Ser Ser Leu Tyr Leu Ala Ala Leu Leu Ser
                     85                  90                  95

Ser Leu Val Ala Ser Thr Ile Thr Arg Arg Phe Gly Arg Lys Leu Ser
             100                 105                 110

Met Leu Phe Gly Gly Leu Leu Phe Leu Val Gly Ala Leu Ile Asn Gly
             115                 120                 125

Phe Ala Asn His Val Trp Met Leu Ile Val Gly Arg Ile Leu Leu Gly
             130                 135                 140

Phe Gly Ile Gly Phe Ala Asn Gln Pro Val Pro Leu Tyr Leu Ser Glu
145                 150                 155                 160

Met Ala Pro Tyr Lys Tyr Arg Gly Ala Leu Asn Ile Gly Phe Gln Leu
                 165                 170                 175

Ser Ile Thr Ile Gly Ile Leu Val Ala Asn Val Leu Asn Tyr Phe Phe
             180                 185                 190

Ala Lys Ile Lys Gly Gly Trp Gly Trp Arg Leu Ser Leu Gly Gly Ala
             195                 200                 205

Met Val Pro Ala Leu Ile Ile Thr Ile Gly Ser Leu Val Leu Pro Asp
     210                 215                 220

Thr Pro Asn Ser Met Ile Glu Arg Gly Asp Arg Asp Gly Ala Lys Ala
225                 230                 235                 240

Gln Leu Lys Arg Ile Arg Gly Ile Glu Asp Val Asp Glu Glu Phe Asn
                 245                 250                 255

Asp Leu Val Ala Ala Ser Glu Ala Ser Met Gln Val Glu Asn Pro Trp
             260                 265                 270

Arg Asn Leu Leu Gln Arg Lys Tyr Arg Pro Gln Leu Thr Met Ala Val
             275                 280                 285

Leu Ile Pro Phe Phe Gln Gln Phe Thr Gly Ile Asn Val Ile Met Phe
     290                 295                 300

Tyr Ala Pro Val Leu Phe Asn Ser Ile Gly Phe Lys Asp Asp Ala Ser
305                 310                 315                 320

Leu Met Ser Ala Val Ile Thr Gly Val Val Asn Val Val Ala Thr Cys
                 325                 330                 335

Val Ser Ile Tyr Gly Val Asp Lys Trp Gly Arg Arg Ala Leu Phe Leu
             340                 345                 350

Glu Gly Gly Ala Gln Met Leu Ile Cys Gln Val Ala Val Ala Ala Ala
             355                 360                 365

Ile Gly Ala Lys Phe Gly Thr Ser Gly Asn Pro Gly Asn Leu Pro Glu
     370                 375                 380

Trp Tyr Ala Ile Val Val Leu Phe Ile Cys Ile Tyr Val Ala Gly Phe
385                 390                 395                 400

Phe Ala Trp Ser Trp Gly Pro Leu Gly Trp Leu Val Pro Ser Glu Ile
                 405                 410                 415

Phe Pro Leu Glu Ile Arg Ser Ala Ala Gln Ser Val Asn Val Ser Val
             420                 425                 430

Asn Met Leu Phe Thr Phe Leu Val Ala Gln Val Phe Leu Ile Met Leu
             435                 440                 445

Cys His Met Lys Phe Gly Leu Phe Leu Phe Phe Ala Phe Phe Val Leu
     450                 455                 460

Val Met Ser Ile Tyr Val Phe Phe Leu Leu Pro Glu Thr Lys Gly Ile
```

```
                465                 470                 475                 480
Pro Ile Glu Glu Met Asp Arg Val Trp Lys Ser His Pro Phe Trp Ser
                    485                 490                 495

Arg Phe Val Glu His Gly Asp His Gly Asn Gly Val Glu Met Gly Lys
                500                 505                 510

Gly Ala Pro Lys Asn Val
            515

<210> SEQ ID NO 24
<211> LENGTH: 519
<212> TYPE: PRT
<213> ORGANISM: Vitis vinifera

<400> SEQUENCE: 24

Met Pro Ala Val Gly Gly Phe Asp Lys Gly Thr Gly Lys Ala Tyr Pro
  1               5                  10                  15

Gly Asn Leu Thr Pro Tyr Val Thr Val Thr Cys Val Val Ala Ala Met
                 20                  25                  30

Gly Gly Leu Ile Phe Gly Tyr Asp Ile Gly Ile Ser Gly Gly Val Thr
             35                  40                  45

Ser Met Ala Pro Phe Leu Gln Lys Phe Phe Pro Ser Val Tyr Arg Lys
 50                  55                  60

Glu Ala Leu Asp Lys Ser Thr Asn Gln Tyr Cys Lys Phe Asp Ser Glu
 65                  70                  75                  80

Thr Leu Thr Leu Phe Thr Ser Ser Leu Tyr Leu Ala Ala Leu Leu Ser
                 85                  90                  95

Ser Leu Val Ala Ala Thr Val Thr Arg Lys Phe Gly Arg Lys Leu Ser
            100                 105                 110

Met Leu Phe Gly Gly Leu Leu Phe Cys Ala Gly Ala Ile Ile Asn Gly
        115                 120                 125

Ala Ala Lys Ala Val Trp Met Leu Ile Val Gly Arg Ile Leu Leu Gly
130                 135                 140

Phe Gly Ile Gly Phe Ala Asn Gln Ser Val Pro Leu Tyr Leu Ser Glu
145                 150                 155                 160

Met Ala Pro Tyr Lys Tyr Arg Gly Ala Leu Asn Ile Gly Phe Gln Leu
                165                 170                 175

Ser Ile Thr Ile Gly Ile Leu Val Ala Asn Ile Leu Asn Tyr Phe Phe
            180                 185                 190

Ala Lys Ile Lys Gly Gly Trp Gly Trp Arg Leu Ser Leu Gly Gly Ala
        195                 200                 205

Val Val Pro Ala Leu Ile Ile Thr Val Gly Ser Leu Val Leu Pro Asp
210                 215                 220

Thr Pro Asn Ser Met Ile Glu Arg Gly Gln His Glu Gly Ala Lys Thr
225                 230                 235                 240

Lys Leu Arg Arg Ile Arg Gly Val Asp Asp Val Glu Glu Glu Phe Asn
                245                 250                 255

Asp Leu Val Val Ala Ser Glu Ala Ser Lys Leu Val Glu His Pro Trp
            260                 265                 270

Arg Asn Leu Leu Gln Arg Lys Tyr Arg Pro His Leu Thr Met Ala Ile
        275                 280                 285

Leu Ile Pro Phe Phe Gln Gln Leu Thr Gly Ile Asn Val Ile Met Phe
290                 295                 300

Tyr Ala Pro Val Leu Phe Lys Thr Ile Gly Phe Ala Asp Asp Ala Ser
305                 310                 315                 320
```

```
-continued

Leu Met Ser Ala Val Ile Thr Gly Gly Val Asn Val Leu Ala Thr Ile
                325                 330                 335

Val Ser Ile Tyr Gly Val Asp Lys Trp Gly Arg Arg Phe Leu Phe Leu
                340                 345                 350

Glu Gly Gly Thr Gln Met Leu Ile Cys Gln Val Ile Val Ala Thr Cys
            355                 360                 365

Ile Gly Val Lys Phe Gly Val Asp Gly Glu Pro Gly Ala Leu Pro Lys
        370                 375                 380

Trp Tyr Ala Ile Val Val Val Leu Phe Ile Cys Val Tyr Val Ser Gly
385                 390                 395                 400

Phe Ala Trp Ser Trp Gly Pro Leu Gly Trp Leu Val Pro Ser Glu Ile
                405                 410                 415

Phe Pro Leu Glu Ile Arg Ser Ala Ala Gln Ser Val Asn Val Ser Val
                420                 425                 430

Asn Met Phe Phe Thr Phe Ile Ile Ala Gln Ile Phe Leu Asn Met Leu
            435                 440                 445

Cys His Met Lys Phe Gly Leu Phe Leu Phe Phe Ala Phe Phe Val Val
        450                 455                 460

Val Met Ser Phe Phe Ile Tyr Phe Phe Leu Pro Glu Thr Lys Gly Ile
465                 470                 475                 480

Pro Ile Glu Glu Met Ala Glu Val Trp Lys Ser His Trp Phe Trp Ser
                485                 490                 495

Arg Tyr Val Asn Asp Gly Ser Tyr Ser Gly Val Glu Leu Val Lys Glu
            500                 505                 510

Asn Tyr Pro Val Lys Asn Val
            515
```

HEXOSE CARRIER PROTEINS

CROSS-REFERENCE TO RELATED APPLICATIONS

This application is a continuation of International Application No. PCT/US99/07561 filed Apr. 7, 1999, now pending, which claims priority benefit of U.S. Provisional Application No. 60/081,131 filed Apr. 9, 1998.

FIELD OF THE INVENTION

This invention is in the field of plant molecular biology. More specifically, this invention pertains to nucleic acid fragments encoding hexose carrier proteins in plants and seeds.

BACKGROUND OF THE INVENTION

In plants, there is a compartmentation of metabolism between the cytosol and the plastid; the chloroplast envelope is in part responsible for this compartmentalization. This envelope or membrane selectively transports free hexose sugars including D-glucose, D-fructose and D-ribose. Hexose carrier proteins, situated in the chloroplast membrane, are responsible for controlling the flux of carbon, in the form of hexose sugars, across the envelop. Hexose carrier proteins may be used to manipulate carbohydrate transport and may be used to alter carbon partioning in the whole plant or to manipulate carbohydrate distribution between cellular compartments.

No corn, rice, sorghum, soybean, or wheat genes have been reported for any hexose carrier protein. Accordingly, the availability of nucleic acid sequences encoding all or a portion of these enzymes would facilitate studies to better understand carbohydrate metabolism and function in plants, provide genetic tools for the manipulation of these biosynthetic pathways, and provide a means to control carbohydrate transport and distribution in plant cells.

SUMMARY OF THE INVENTION

The instant invention relates to isolated nucleic acid fragments encoding hexose carrier proteins. Specifically, this invention concerns an isolated nucleic acid fragment encoding a corn, rice, sorghum, soybean or wheat hexose carrier protein. In addition, this invention relates to a nucleic acid fragment that is complementary to the nucleic acid fragment encoding a corn, rice, sorghum, soybean or wheat hexose carrier protein. An additional embodiment of the instant invention pertains to a polypeptide encoding all or a substantial portion of a corn, rice, sorghum, soybean or wheat hexose carrier protein.

In another embodiment, the instant invention relates to a chimeric gene encoding a corn, rice, sorghum, soybean or wheat hexose carrier protein, or to a chimeric gene that comprises a nucleic acid fragment that is complementary to a nucleic acid fragment encoding a corn, rice, sorghum, soybean or wheat hexose carrier protein, operably linked to suitable regulatory sequences, wherein expression of the chimeric gene results in production of levels of the encoded protein in a transformed host cell that is altered (i.e., increased or decreased) from the level produced in an untransformed host cell.

In a further embodiment, the instant invention concerns a transformed host cell comprising in its genome a chimeric gene encoding a corn, rice, sorghum, soybean or wheat hexose carrier protein, operably linked to suitable regulatory sequences. Expression of the chimeric gene results in production of altered levels of the encoded protein in the transformed host cell. The transformed host cell can be of eukaryotic or prokaryotic origin, and include cells derived from higher plants and microorganisms. The invention also includes transformed plants that arise from transformed host cells of higher plants, and seeds derived from such transformed plants.

An additional embodiment of the instant invention concerns a method of altering the level of expression of a corn, rice, sorghum, soybean or wheat hexose carrier protein in a transformed host cell comprising: a) transforming a host cell with a chimeric gene comprising a nucleic acid fragment encoding a corn, rice, sorghum, soybean or wheat hexose carrier protein; and b) growing the transformed host cell under conditions that are suitable for expression of the chimeric gene wherein expression of the chimeric gene results in production of altered levels of hexose carrier protein in the transformed host cell.

An addition embodiment of the instant invention concerns a method for obtaining a nucleic acid fragment encoding all or a substantial portion of an amino acid sequence encoding a corn, rice, sorghum, soybean or wheat hexose carrier protein.

BRIEF DESCRIPTION OF THE DRAWINGS AND SEQUENCE DESCRIPTIONS

The invention can be more fully understood from the following detailed description and the accompanying drawing and Sequence Listing which form a part of this application.

FIGS. 1A, 1B, 1C, 1D and 1E present an alignment of the amino acid sequences set forth in SEQ ID NOs:2, 4, 6, 8, 10, 12, 14, 16 and 18 and the *Arabidopsis thaliana* (SEQ ID NOs:22 and 23), *Medicago truncatula* (SEQ IN NO:24), *Ricinus communis* (SEQ ID NO:19) and Saccharum sp. (SEQ ID NO:20) hexose carrier protein sequences. The alignment was constructed using the Clustal algorithm.

The following sequence descriptions and Sequence Listing attached hereto comply with the rules governing nucleotide and/or amino acid sequence disclosures in patent applications as set forth in 37 C.F.R. §1.821–1.825.

SEQ ID NO:1 is the nucleotide sequence comprising a contig assembled from the cDNA inserts in clones cc71sea.pk0002.d11, p0134.caras06r and p0045.ckdaa62r encoding 98% of a corn hexose carrier protein.

SEQ ID NO:2 is the deduced amino acid sequence of a portion of a hexose carrier protein derived from the nucleotide sequence of SEQ ID NO:1.

SEQ ID NO:3 is the nucleotide sequence comprising a portion of the cDNA insert in clone ccase-b.pk0007.g12 encoding a portion of a corn hexose carrier protein.

SEQ ID NO:4 is the deduced amino acid sequence of a portion of a hexose carrier protein derived from the nucleotide sequence of SEQ ID NO:3.

SEQ ID NO:5 is the nucleotide sequence comprising the entire cDNA insert in clone crl.pk0030.c3 encoding a portion of a corn hexose carrier protein.

SEQ ID NO:6 is the deduced amino acid sequence of a portion of a hexose carrier protein derived from the nucleotide sequence of SEQ ID NO:5.

SEQ ID NO:7 is the nucleotide sequence comprising a portion of the cDNA insert in clone m.15.12.d09.sk20 encoding a portion of a corn hexose carrier protein.

SEQ ID NO:8 is the deduced amino acid sequence of a portion of a hexose carrier protein derived from the nucleotide sequence of SEQ ID NO:7.

SEQ ID NO:9 is the nucleotide sequence comprising a contig assembled form the cDNA inserts in clones rls6.pk0032.h11 and rlr12.pk0010.f3 encoding a portion of a rice hexose carrier protein.

SEQ ID NO:10 is the deduced amino acid sequence of a portion of a hexose carrier protein derived from the nucleotide sequence of SEQ ID NO:9.

SEQ ID NO:11 is the nucleotide sequence comprising a contig assembled form the cDNA inserts in clones rlr6.pk0090.d4 and rls6.pk0083.g4 encoding an entire rice hexose carrier protein.

SEQ ID NO:12 is the deduced amino acid sequence of an entire hexose carrier protein derived from the nucleotide sequence of SEQ ID NO:11.

SEQ ID NO:13 is the nucleotide sequence comprising the entire cDNA insert in clone sgr16.pk0001.h4 encoding a portion of a sorghum hexose carrier protein.

SEQ ID NO:14 is the deduced amino acid sequence of a portion of a hexose carrier protein derived from the nucleotide sequence of SEQ ID NO:13.

SEQ ID NO:15 is the nucleotide sequence comprising a contig assembled from the cDNA inserts in clones sfl1.pk0028.a10, sfl1.pk133.j5 and sgc5c.pk001.h24 encoding an entire soybean hexose carrier protein.

SEQ ID NO:16 is the deduced amino acid sequence of an entire hexose carrier protein derived from the nucleotide sequence of SEQ ID NO:15.

SEQ ID NO:17 is the nucleotide sequence comprising the entire cDNA insert in clone wlk8.pk0016.c6 encoding an entire wheat hexose carrier protein.

SEQ ID NO:18 is the deduced amino acid sequence of an entire hexose carrier protein derived from the nucleotide sequence of SEQ ID NO:17.

SEQ ID NO:19 is the amino acid sequence of a *Ricinus communis* (NCBI Identifier No. gi 1708191) hexose carrier protein.

SEQ ID NO:20 is the amino acid sequence of a Saccharum species (NCBI Identifier No. gi 347853) hexose carrier protein.

SEQ ID NO:21 is the amino acid sequence of an *Arabidopsis thaliana* (NCBI Identifier No. gi 3540199) hexose carrier protein.

SEQ ID NO:22 is the amino acid sequence of an *Arabidopsis thaliana* (NCBI Identifier No. gi 99758) hexose carrier protein.

SEQ ID NO:23 is the amino acid sequence of a *Medicago truncatula* (NCBI Identifier No. gi 1353516) hexose carrier protein.

SEQ ID NO:24 is the amino acid sequence of a *Vitis vinifera* (NCBI Identifier No. gi 4138724) hexose carrier protein.

The Sequence Listing contains the one letter code for nucleotide sequence characters and the three letter codes for amino acids as defined in conformity with the IUPAC-IUBMB standards described in *Nucleic Acids Research* 13:3021–3030 (1985) and in the *Biochemical Journal* 219 (No. 2):345–373 (1984) which are herein incorporated by reference. The symbols and format used for nucleotide and amino acid sequence data comply with the rules set forth in 37 C.F.R. §1.822.

DETAILED DESCRIPTION OF THE INVENTION

In the context of this disclosure, a number of terms shall be utilized. As used herein, an "isolated nucleic acid fragment" is a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA. As used herein, "contig" refers to an assemblage of overlapping nucleic acid sequences to form one contiguous nucleotide sequence. For example, several DNA sequences can be compared and aligned to identify common or overlapping regions. The individual sequences can then be assembled into a single contiguous nucleotide sequence.

As used herein, "substantially similar" refers to nucleic acid fragments wherein changes in one or more nucleotide bases results in substitution of one or more amino acids, but do not affect the functional properties of the protein encoded by the DNA sequence.

"Substantially similar" also refers to nucleic acid fragments wherein changes in one or more nucleotide bases does not affect the ability of the nucleic acid fragment to mediate alteration of gene expression by antisense or co-suppression technology. "Substantially similar" also refers to modifications of the nucleic acid fragments of the instant invention such as deletion or insertion of one or more nucleotides that do not substantially affect the functional properties of the resulting transcript vis-à-vis the ability to mediate alteration of gene expression by antisense or co-suppression technology or alteration of the functional properties of the resulting protein molecule. It is therefore understood that the invention encompasses more than the specific exemplary sequences.

For example, it is well known in the art that antisense suppression and co-suppression of gene expression may be accomplished using nucleic acid fragments representing less than the entire coding region of a gene, and by nucleic acid fragments that do not share 100% sequence identity with the gene to be suppressed. Moreover, alterations in a gene which result in the production of a chemically equivalent amino acid at a given site, but do not effect the functional properties of the encoded protein, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the protein molecule would also not be expected to alter the activity of the protein. Each of the proposed modifications is well within the routine skill in the art, as is determination of retention of biological activity of the encoded products.

Moreover, substantially similar nucleic acid fragments may also be characterized by their ability to hybridize, under stringent conditions (0.1×SSC, 0.1% SDS, 65° C.), with the nucleic acid fragments disclosed herein.

Substantially similar nucleic acid fragments of the instant invention may also be characterized by the percent similarity of the amino acid sequences that they encode to the amino acid sequences disclosed herein, as determined by algorithms commonly employed by those skilled in this art. Preferred are those nucleic acid fragments whose nucleotide sequences encode amino acid sequences that are 95% similar to the amino acid sequences reported herein. Sequence alignments and percent similarity calculations were performed using the Megalign program of the LASARGENE bioinformatics computing suite (DNASTAR Inc., Madison, Wis.). Multiple alignment of the sequences was performed using the Clustal method of alignment (Higgins, D. G. and Sharp, P. M. (1989) CABIOS. 5:151–153) with the default parameters (GAP PENALTY=10, GAP LENGTH PENALTY=10), (hereafter Clustal algorithm). Default parameters for pairwise alignments using the Clustal method were KTUPLE 1, GAP PENALTY=3, WINDOW=5 and DIAGONALS SAVED=5.

A "substantial portion" of an amino acid or nucleotide sequence comprises enough of the amino acid sequence of a polypeptide or the nucleotide sequence of a gene to afford putative identification of that polypeptide or gene, either by manual evaluation of the sequence by one skilled in the art, or by computer-automated sequence comparison and identification using algorithms such as BLAST (Basic Local Alignment Search Tool; Altschul, S. F., et al., (1993) *J. Mol. Biol.* 215:403–410). In general, a sequence of ten or more contiguous amino acids or thirty or more nucleotides is necessary in order to putatively identify a polypeptide or nucleic acid sequence as homologous to a known protein or gene. Moreover, with respect to nucleotide sequences, gene specific oligonucleotide probes comprising 20–30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12–15 bases may be used as amplification primers in PCR in order to obtain a particular nucleic acid fragment comprising the primers. Accordingly, a "substantial portion" of a nucleotide sequence comprises enough of the sequence to afford specific identification and/or isolation of a nucleic acid fragment comprising the sequence. The instant specification teaches partial or complete amino acid and nucleotide sequences encoding one or more particular plant proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

"Codon degeneracy" refers to divergence in the genetic code permitting variation of the nucleotide sequence without effecting the amino acid sequence of an encoded polypeptide. Accordingly, the instant invention relates to any nucleic acid fragment that encodes all or a substantial portion of the amino acid sequence encoding the corn, rice, sorghum, soybean or wheat hexose carrier proteins as set forth in SEQ ID NOs:2, 4, 6, 8, 10, 12, 14, 16 and 18. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

"Synthetic genes" can be assembled from oligonucleotide building blocks that are chemically synthesized using procedures known to those skilled in the art. These building blocks are ligated and annealed to form gene segments which are then enzymatically assembled to construct the entire gene. "Chemically synthesized", as related to a sequence of DNA, means that the component nucleotides were assembled in vitro. Manual chemical synthesis of DNA may be accomplished using well established procedures, or automated chemical synthesis can be performed using one of a number of commercially available machines. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a DNA sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a DNA sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a DNA sequence which can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. Promoters which cause a gene to be expressed in most cell types at most times are commonly referred to as "constitutive promoters". New promoters of various types useful in plant cells are constantly being discovered; numerous examples may be found in the compilation by Okamuro and Goldberg, (1989) *Biochemistry of Plants* 15:1–82. It is further recognized that since in most cases the exact boundaries of regulatory sequences have not been completely defined, DNA fragments of different lengths may have identical promoter activity.

The "translation leader sequence" refers to a DNA sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner, R. and Foster, G. D. (1995) *Molecular Biotechnology* 3:225).

The "3' non-coding sequences" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al., (1989) *Plant Cell* 1:671–680.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and that can be translated into protein by the cell. "cDNA" refers to a double-stranded DNA that is complementary to and derived from mRNA. "Sense" RNA refers to RNA transcript that includes the mRNA and so can be translated into protein by the cell. "Antisense RNA" refers to a RNA transcript that is complementary to all or part of a target primary transcript or mRNA and that blocks the expression of a target gene (U.S. Pat. No. 5,107,065, incorporated herein by reference). The complementarity of an antisense RNA may be with any part of the specific gene transcript, i.e., at the 5' non-coding sequence, 3' non-coding sequence, introns, or the coding sequence. "Functional RNA" refers to sense RNA, antisense RNA, ribozyme RNA, or other RNA that may not be translated but yet has an effect on cellular processes.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020, incorporated herein by reference).

"Altered levels" refers to the production of gene product (s) in transgenic organisms in amounts or proportions that differ from that of normal or non-transformed organisms.

"Mature" protein refers to a post-translationally processed polypeptide; i.e., one from which any pre- or propeptides present in the primary translation product have been removed. "Precursor" protein refers to the primary product of translation of mRNA; i.e., with pre- and propeptides still present. Pre- and propeptides may be but are not limited to intracellular localization signals.

A "chloroplast transit peptide" is an amino acid sequence which is translated in conjunction with a protein and directs the protein to the chloroplast or other plastid types present in the cell in which the protein is made. "Chloroplast transit sequence" refers to a nucleotide sequence that encodes a chloroplast transit peptide. A "signal peptide" is an amino acid sequence which is translated in conjunction with a protein and directs the protein to the secretory system (Chrispeels, J. J., (1991) *Ann. Rev. Plant Phys. Plant Mol. Biol.* 42:21–53). If the protein is to be directed to a vacuole, a vacuolar targeting signal (supra) can further be added, or if to the endoplasmic reticulum, an endoplasmic reticulum retention signal (supra) may be added. If the protein is to be directed to the nucleus, any signal peptide present should be removed and instead a nuclear localization-signal included (Raikhel (1992) *Plant Phys.* 100:1627–1632).

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include Agrobacterium-mediated transformation (De Blaere et al. (1987) *Meth. Enzymol.* 143:277) and particle-accelerated or "gene gun" transformation technology (Klein et al. (1987) *Nature (London)* 327:70–73; U.S. Pat. No. 4,945,050, incorporated herein by reference).

Standard recombinant DNA and molecular cloning techniques used herein are well known in the art and are described more fully in Sambrook, J., Fritsch, E. F. and Maniatis, T. *Molecular Cloning: A Laboratory Manual;* Cold Spring Harbor Laboratory Press: Cold Spring Harbor, 1989 (hereinafter "Maniatis").

Nucleic acid fragments encoding at least a portion of several hexose carrier proteins have been isolated and identified by comparison of random plant cDNA sequences to public databases containing nucleotide and protein sequences using the BLAST algorithms well known to those skilled in the art. Table 1 lists the proteins that are described herein, and the designation of the cDNA clones that comprise the nucleic acid fragments encoding these proteins.

TABLE 1

| Hexose Carrier Proteins | | |
| --- | --- | --- |
| Enzyme | Clone | Plant |
| Hexose Carrier Proteins | cc71sea.pk0002.d11 | Corn |
| | p0134.caras06r | Corn |
| | p0045.ckdaa62r | Corn |
| | ccase-b.pk0007.g12 | Corn |
| | crl.pk0030.c3 | Corn |
| | m.15.12.d09.sk20 | Corn |
| | rlr6.pk0090.d4 | Rice |
| | rls6.pk0083.g4 | Rice |
| | rls6.pk0032.h11 | Rice |
| | rlr12.pk0010.f3 | Rice |
| | sgr16.pk0001.h4 | Sorghum |
| | sfl1.pk0028.a10 | Soybean |
| | sfl1.pk133.j5 | Soybean |
| | sgc5c.pk001.h24 | Soybean |
| | wlk8.pk0016.c6 | Soybean |

The nucleic acid fragments of the instant invention may be used to isolate cDNAs and genes encoding homologous proteins from the same or other plant species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction).

For example, genes encoding other hexose carrier proteins, either as cDNAs or genomic DNAs, could be isolated directly by using all or a portion of the instant nucleic acid fragments as DNA hybridization probes to screen libraries from any desired plant employing methodology well known to those skilled in the art. Specific oligonucleotide probes based upon the instant nucleic acid sequences can be designed and synthesized by methods known in the art (Maniatis). Moreover, the entire sequences can be used directly to synthesize DNA probes by methods known to the skilled artisan such as random primer DNA labeling, nick translation, or end-labeling techniques, or RNA probes using available in vitro transcription systems. In addition, specific primers can be designed and used to amplify a part or all of the instant sequences. The resulting amplification products can be labeled directly during amplification reactions or labeled after amplification reactions, and used as probes to isolate full length cDNA or genomic fragments under conditions of appropriate stringency.

In addition, two short segments of the instant nucleic acid fragments may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding plant genes. Alternatively, the second primer sequence may be based upon sequences derived from the cloning vector. For example, the skilled artisan can follow the RACE protocol (Frohman et al., (1988) *PNAS USA* 85:8998) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al., (1989) *PNAS USA* 86:5673; Loh et al., (1989) *Science* 243:217). Products generated by the 3' and 5' RACE procedures can be combined to generate full-length cDNAs (Frohman, M. A. and Martin, G. R., (1989) *Techniques* 1:165).

Availability of the instant nucleotide and deduced amino acid sequences facilitates immunological screening of cDNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen cDNA expression libraries to isolate full-length cDNA clones of interest (Lerner, R. A. (1984) *Adv. Immunol.* 36:1; Maniatis).

The nucleic acid fragments of the instant invention may be used to create transgenic plants in which the disclosed corn, rice, sorghum, soybean or wheat hexose carrier proteins are present at higher or lower levels than normal or in cell types or developmental stages in which they are not normally found. This would have the effect of altering the flux of carbon to various cellular compartments in those cells.

Overexpression of the corn, rice, sorghum, soybean and wheat hexose carrier proteins of the instant invention may be accomplished by first constructing a chimeric gene in which the coding region is operably linked to a promoter capable of directing expression of a gene in the desired tissues at the desired stage of development. For reasons of convenience, the chimeric gene may comprise promoter sequences and translation leader sequences derived from the same genes. 3' Non-coding sequences encoding transcription termination signals may also be provided. The instant chimeric gene may also comprise one or more introns in order to facilitate gene expression.

Plasmid vectors comprising the instant chimeric gene can then constructed. The choice of plasmid vector is dependent upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al., (1985) *EMBO J.* 4:2411–2418; De Almeida et al., (1989) *Mol. Gen. Genetics* 218:78–86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

For some applications it may be useful to direct the instant hexose carrier proteins to different cellular compartments, or to facilitate its secretion from the cell. It is thus envisioned that the chimeric gene described above may be further supplemented by altering the coding sequence to encode a corn, rice, sorghum, soybean or wheat hexose carrier protein with appropriate intracellular targeting sequences such as transit sequences (Keegstra, K. (1989) *Cell* 56:247–253), signal sequences or sequences encoding endoplasmic reticulum localization (Chrispeels, J. J., (1991) *Ann. Rev. Plant Phys. Plant Mol. Biol.* 42:21–53), or nuclear localization signals (Raikhel, N. (1992) *Plant Phys.* 100:1627–1632) added and/or with targeting sequences that are already present removed. While the references cited give examples of each of these, the list is not exhaustive and more targeting signals of utility may be discovered in the future.

It may also be desirable to reduce or eliminate expression of genes encoding corn, rice, sorghum, soybean or wheat hexose carrier proteins in plants for some applications. In order to accomplish this, a chimeric gene designed for co-suppression of the instant hexose carrier proteins can be constructed by linking a gene or gene fragment encoding a corn, rice, sorghum, soybean or wheat hexose carrier protein to plant promoter sequences. Alternatively, a chimeric gene designed to express antisense RNA for all or part of the instant nucleic acid fragment can be constructed by linking the gene or gene fragment in reverse orientation to plant promoter sequences. Either the co-suppression or antisense chimeric genes could be introduced into plants via transformation wherein expression of the corresponding endogenous genes are reduced or eliminated.

The instant corn, rice, sorghum, soybean and wheat hexose carrier proteins (or portions thereof) may be produced in heterologous host cells, particularly in the cells of microbial hosts, and can be used to prepare antibodies to the these proteins by methods well known to those skilled in the art. The antibodies are useful for detecting hexose carrier protein in situ in cells or in vitro in cell extracts. Preferred heterologous host cells for production of the instant corn, rice, sorghum, soybean or wheat hexose carrier proteins are microbial hosts. Microbial expression systems and expression vectors containing regulatory sequences that direct high level expression of foreign proteins are well known to those skilled in the art. Any of these could be used to construct a chimeric gene for production of the instant corn, rice, sorghum, soybean or wheat hexose carrier proteins. This chimeric gene could then be introduced into appropriate microorganisms via transformation to provide high level expression of the encoded hexose carrier protein. An example of a vector for high level expression of the instant corn, rice, sorghum, soybean or wheat hexose carrier proteins in a bacterial host is provided (Example 6).

All or a substantial portion of the nucleic acid fragments of the instant invention may also be used as probes for genetically and physically mapping the genes that they are a part of, and as markers for traits linked to those genes. Such information may be useful in plant breeding in order to develop lines with desired phenotypes. For example, the instant nucleic acid fragments may be used as restriction fragment length polymorphism (RFLP) markers. Southern blots (Maniatis) of restriction-digested plant genomic DNA may be probed with the nucleic acid fragments of the instant invention. The resulting banding patterns may then be subjected to genetic analyses using computer programs such as MapMaker (Lander et al., (1987) *Genomics* 1:174–181) in order to construct a genetic map. In addition, the nucleic acid fragments of the instant invention may be used to probe Southern blots containing restriction endonuclease-treated genomic DNAs of a set of individuals representing parent and progeny of a defined genetic cross. Segregation of the DNA polymorphisms is noted and used to calculate the position of the instant nucleic acid sequence in the genetic map previously obtained using this population (Botstein, D. et al., (1980) *Am. J. Hum. Genet.* 32:314–331).

The production and use of plant gene-derived probes for use in genetic mapping is described in R. Bernatzky, R. and Tanksley, S. D. (1986) *Plant Mol. Biol. Reporter* 4(1):37–41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

Nucleic acid probes derived from the instant nucleic acid sequences may also be used for physical mapping (i.e., placement of sequences on physical maps; see Hoheisel, J. D., et al., In: *Nonmammalian Genomic Analysis: A Practical Guide,* Academic press 1996, pp. 319–346, and references cited therein).

In another embodiment, nucleic acid probes derived from the instant nucleic acid sequences may be used in direct fluorescence in situ hybridization (FISH) mapping (Trask, B. J. (1991) *Trends Genet.* 7:149–154). Although current methods of FISH mapping favor use of large clones (several to several hundred KB; see Laan, M. et al. (1995) *Genome Research* 5:13–20), improvements in sensitivity may allow performance of FISH mapping using shorter probes.

A variety of nucleic acid amplification-based methods of genetic and physical mapping may be carried out using the instant nucleic acid sequences. Examples include allele-specific amplification (Kazazian, H. H. (1989) *J. Lab. Clin. Med.* 114(2):95–96), polymorphism of PCR-amplified fragments (CAPS; Sheffield, V. C. et al. (1993) *Genomics* 16:325–332), allele-specific ligation (Landegren, U. et al. (1988) *Science* 241:1077–1080), nucleotide extension reactions (Sokolov, B. P. (1990) *Nucleic Acid Res.* 18:3671), Radiation Hybrid Mapping (Walter, M. A. et al. (1997) *Nature Genetics* 7:22–28) and Happy Mapping (Dear, P. H. and Cook, P. R. (1989) *Nucleic Acid Res.* 17:6795–6807). For these methods, the sequence of a nucleic acid fragment is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

Loss of function mutant phenotypes may be identified for the instant cDNA clones either by targeted gene disruption protocols or by identifying specific mutants for these genes contained in a maize population carrying mutations in all possible genes (Ballinger and Benzer, (1989) *Proc. Natl. Acad. Sci USA* 86:9402; Koes et al., (1995) *Proc. Natl. Acad. Sci USA* 92:8149; Bensen et al., (1995) *Plant Cell* 7:75). The latter approach may be accomplished in two ways. First, short segments of the instant nucleic acid fragments may be used in polymerase chain reaction protocols in conjunction with a mutation tag sequence primer on DNAs prepared from a population of plants in which Mutator transposons or some other mutation-causing DNA element has been introduced (see Bensen, supra). The amplification of a specific DNA fragment with these primers indicates the insertion of the mutation tag element in or near the plant gene encoding the hexose carrier protein. Alternatively, the instant nucleic acid fragment may be used as a hybridization probe against PCR amplification products generated from the mutation population using the mutation tag sequence primer in conjunction with an arbitrary genomic site primer, such as that for a restriction enzyme site-anchored synthetic adaptor. With either method, a plant containing a mutation in the endogenous gene encoding a hexose carrier protein can be identified and obtained. This mutant plant can then be used to determine or confirm the natural function of the hexose carrier protein gene product.

EXAMPLES

The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

Example 1

Composition of cDNA Libraries; Isolation and Sequencing of cDNA Clones cDNA libraries representing mRNAs from various corn, rice, sorghum, soybean and wheat tissues were prepared. The characteristics of the libraries are described below.

TABLE 2 cDNA Libraries from Corn, Rice, Sorghum, Soybean or Wheat

| Library | Tissue | Clone |
| --- | --- | --- |
| cc71se-a | Corn (*Zea mays* L.) type II callus tissue, somatic embryo formed | cc71se-a.pk0002.d11 |
| ccase-b | Corn (*Zea mays* L.) type II callus tissue, somatic embryo formed, highly transformable | ccase-b.pk0007.g12 |
| cr1 | Corn (*Zea mays* L.) root from 7 day seedlings grown in light | cr1.pk0030.c3 |
| m.15 | Corn (*Zea mays* L.) 15 day old embryo | m.15.12.d09.sk20 |
| p0045 | Corn HI-II suspension culture cell line | p0045.ckdaa62r |
| p0134 | Corn HI-II callus, regeneration of tissue for 5 to 15 days, tissue cultures then pooled | p0134.caras06r |
| rlr6 | Rice (*Oryza sativa* L.) leaf (15 DAG) 6 hrs after infection of *Magaporthe grisea* strain 4360-R-62 (AVR2-YAMO); Resistant | rlr6.pk0090.d4 |
| rlr12 | Rice (*Oryza sativa* L.) leaf (15 days after germination) 12 hrs after infection of *Magaporthe grisea* strain 4360-R-67 (avr2-yamo); Susceptible | rlr12.pk0010.f3 |
| rls6 | Rice (*Oryza sativa* L.) leaf (15 days after germination)\ 6 hrs after infection of *Magaporthe grisea* strain 4360-R-67 (avr2-yamo); Susceptible | rls6.pk0083.g4<br>rls6.pk0032.h11 |
| sfl1 | Soybean (*Glycine max* L.) immature flower | sfl1.pk0028.a10<br>sfl1.pk133.j5 |
| sgc5c | Soybean (*Glycine max* L., Wye) germinating cotyledon (¾ yellow; 15–24 days after germination) | sgc5c.pk001.h24 |
| sgr16 | Sorghum 11 day-low dhurrin | sgr16.pk0001.h4 |
| wlk8 | Wheat (*Triticum aestivum* L.) seedlings 8 hr after treatment with fungicide* | wlk8.pk0016.c6 |

*Application of 6-iodo-2-propoxy-3-propyl-4(3H)-quinazolinone; synthesis and methods of using this compound are described in U.S. Ser. No. 08/545,827, incorporated herein by reference.

cDNA libraries were prepared in Uni-ZAP™ XR vectors according to the manufacturer's protocol (Stratagene Cloning Systems, La Jolla, Calif.). Conversion of the Uni-ZAP™ XR libraries into plasmid libraries was accomplished according to the protocol provided by Stratagene. Upon conversion, cDNA inserts were contained in the plasmid vector pBluescript. cDNA inserts from randomly picked bacterial colonies containing recombinant pBluescript plasmids were amplified via polymerase chain reaction using primers specific for vector sequences flanking the inserted cDNA sequences or plasmid DNA was prepared from cultured bacterial cells. Amplified insert DNAs or plasmid DNAs were sequenced in dye-primer sequencing reactions to generate partial cDNA sequences (expressed sequence tags or "ESTs"; see Adams, M. D. et al., (1991) *Science* 252:1651). The resulting ESTs were analyzed using a Perkin Elmer Model 377 fluorescent sequencer.

Example 2

Identification of cDNA Clones

ESTs encoding hexose carrier proteins were identified by conducting BLAST (Basic Local Alignment Search Tool; Altschul, S. F., et al., (1993) *J. Mol. Biol.* 215:403–410) searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences obtained in Example 1 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish, W. and States, D. J. (1993) *Nature Genetics* 3:266–272 and Altschul, Stephen F., et al. (1997) *Nucleic Acids Res.* 25:3389–3402) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

Example 3

Characterization of cDNA Clones Encoding Hexose Carrier Proteins

The BLASTX search using the nucleotide sequences from clones cc71sea.pk0002.d11, p0134.caras06r and p0045.ckdaa62r revealed similarity of the proteins encoded by the cDNAs to hexose carrier protein from Arabidopsis thaliana (NCBI Identifier No. gi 99758). The BLASTX search using the nucleotide sequence from clone ccase-b.pk0007.g12, rls6.pk0032.h11, rlr12.pk0010.f3, sfl1.pk0028.a10, sfl1.pk133.j5 and sgc5c.pk001.h24 revealed similarity of the protein encoded by the cDNA to hexose carrier protein from *Medicago truncatula* (NCBI Identifier No. gi 1353516). The BLASTX search using the nucleotide sequences from clones cr1.pk0030.c3 and m.15.12.d09.sk20 revealed similarity of the proteins encoded by the cDNAs to hexose carrier protein from *Ricinus communis* (NCBI Identifier No. gi 1708191). BLASTX search using the nucleotide sequences from clones rlr6.pk0090.d4 and rls6.pk0083.g4 revealed similarity of the proteins encoded by the cDNAs to hexose carrier protein from Saccharum species (sp.) (NCBI Identifier No. gi 347853). The BLASTX search using the nucleotide sequence from clone sgr16.pk0001.h4 revealed similarity of the protein encoded by the cDNA to hexose carrier protein from *Arabidopsis thaliana* (NCBI Identifier No. gi 3540199). BLASTX search using the nucleotide sequence from clone wlk8.pk0016.c6 revealed similarity of the protein encoded by the cDNA to hexose carrier protein from *Vitis vinifera* (NCBI Identifier No. gi 4138724).

In the process of comparing the EST sequences, it was found that corn clones cc71sea.pk0002.d11, p0134.caras06r and p0045.ckdaa62r had overlapping regions of homology. Rice clones rls6.pk0032.h11 and rlr12.pk0010.f3 were also found to have overlapping regions of homology and lastly, soybean clones sfl1.pk0028.a10, sfl1.pk133.j5 and sgc5c.pk001.h24 were shown to have overlapping regions of homology. Using this homology it was possible to align the EST sequences and assemble three individual contigs encoding unique corn, rice and soybean hexose carrier proteins.

The BLAST results for each of the contigs and ESTs are shown in Table 3:

TABLE 3

BLAST Results for Clones Encoding Polypeptides Homologous to *Arabidopsis thaliana, Medicago truncatula, Ricinus communis* and Saccharum sp. Hexose Carrier Proteins

| Clone | BLAST pLog Score |
| --- | --- |
| Contig composed of: | >250.00 |
| cc71sea.pk002.d11 | |
| p0134.caras06r | |
| p0045.ckdaa62r | |
| ccase-b.pk0007.g12 | 58.70 |
| cr1.pk0030.c3 | 36.50 |
| m.15.12.d09.sk20 | 35.00 |
| Contig composed of: | 110.00 |
| rls6.pk0032.h11 | |
| rlr12.pk0010.f3 | |
| Contig composed of: | >250.00 |
| rlr6.pk0090.d4 | |
| rls6.pk0083.g4 | |
| sgr16.pk0001.h4 | 31.10 |
| Contig composed of: | >250.00 |
| sf11.pk0028.a10 | |
| sf11.pk133.j5 | |
| sgc5c.pk001.h24 | |
| wlk8.pk0016.c6 | >250.00 |

The sequence of the corn contig composed of clones cc71sea.pk0002.d11, p0134.caras06r and p0045.ckdaa62r is shown in SEQ ID NO:1; the deduced amino acid sequence of this contig, which represents 98% of the N-terminal region of the protein is shown in SEQ ID NO:2.

The sequence of the cDNA insert in clone ccase-b.pk0007.g12 was determined and is shown in SEQ ID NO:3; the deduced amino acid sequence of this cDNA, which represents 27% of the N-terminal region of the protein, is shown in SEQ ID NO:4.

The sequence of the entire cDNA insert of clone cr1.pk0030.c3 is shown in SEQ ID NO:5; the deduced amino acid sequence, which represents 21% of the C-terminal region of the protein, is shown in SEQ ID NO:6.

The sequence of the cDNA insert in clone m.15.12.d09.sk20 was determined and is shown in SEQ ID NO:7; the deduced amino acid sequence of this cDNA, which represents 25% of the C-terminal region of the protein, is shown in SEQ ID NO:8.

The sequence of the rice contig composed of clones rls6.pk0032.h11 and rlr12.pk0010.f3 is shown in SEQ ID NO:9; the deduced amino acid sequence, which represents 51% of the N-terminal region of the protein, is shown in SEQ ID NO:10.

The sequence of the rice contig composed of clones rlr6.pk0090.d4 and rls6.pk0083.g4 is shown in SEQ ID NO:11; the deduced amino acid sequence, which represents 100% of the protein, is shown in SEQ ID NO:12.

The sequence of the entire cDNA insert in clone sgr16.pk0001.h4 is shown in SEQ ID NO:13; the deduced amino acid sequence, which represents 18% of the C-terminal region of the protein, is shown in SEQ ID NO:14.

The sequence of the soybean contig composed of clones sfl1.pk0028.a10, sfl1.pk133.j5 and sgc5c.pk001.h24 is shown in SEQ ID NO:15; the deduced amino acid sequence, which represents 100% of the protein, is shown in SEQ ID NO:16.

The sequence of the cDNA insert in clone wlk8.pk0016.c6 is shown in SEQ ID NO:17; the deduced amino acid sequence, which represents 100% of the protein, is shown in SEQ ID NO:18.

FIG. 1 presents an alignment of the amino acid sequences set forth in SEQ ID NOs:2, 4, 6, 8, 10, 12, 14, 16 and 18 and the *Arabidopsis thaliana, Medicago truncatula, Ricinus communis* and Saccharum sp. hexose carrier protein sequences using the Clustal algorithm.

The data in Table 4 represents a calculation of the percent similarity of the amino acid sequences set forth in SEQ ID NOs:2, 4, 6, 8, 10, 12, 14, 16 and 18 and the *Arabidopsis thaliana, Medicago truncatula, Ricinus communis* and Saccharum sp. hexose carrier protein sequences using the Clustal algorithm. The percent similarity between SEQ ID NOs:2, 4, 6, 8, 10, 12, 14, 16 and 18 ranged between 10% to 83% as calculated by the Clustal algorithm.

TABLE 4

Percent Identity of Amino Acid Sequences Deduced From the Nucleotide Sequences of cDNA Clones Encoding Polypeptides Homologous to *Arabidopsis thaliana, Medicago truncatula, Ricinus communis* and Saccharum sp. Hexose Carrier Proteins

| Clone | SEQ ID NO. | Percent Identity to NCBI Identifier No. (gi) |
| --- | --- | --- |
| Contig composed of: | 2 | 60% (gi 99758) |
| cc71sea.pk0002.d11 | | |
| p0134.caras06r | | |
| p0045.ckdaa62r | | |
| ccase-b.pk0007.g12 | 4 | 71% (gi 1353516) |
| crl.pk0030.c3 | 6 | 57% (gi 1708191) |
| m.15.12.d09.sk20 | 8 | 48% (gi 1708191) |
| Contig composed of: | 10 | 65% (gi 1353516) |
| rls6.pk0032.h11 | | |
| rlr12.pk0010.f3 | | |
| Contig composed of: | 12 | 90% (gi 347853) |
| rlr6.pk0090.d4 | | |
| rls6.pk0083.g4 | | |
| sgr16.pk0001.h4 | 14 | 54% (gi 3540199) |
| Contig composed of: | 16 | 88% (gi 1353516) |
| sf11.pk0028.a10 | | |
| sf11.pk133.j5 | | |
| sgc5c.pk001.h24 | | |
| wlk8.pk0016.c6 | 18 | 67% (gi 4138724) |

Sequence alignments and BLAST scores and probabilities indicate that the instant nucleic acid fragments encode entire or portions of hexose carrier proteins. These sequences represent the first corn, rice, sorghum, soybean and wheat sequences encoding hexose carrier proteins.

Example 4

Expression of Chimeric Genes in Monocot Cells

A chimeric gene comprising a cDNA encoding a hexose carrier protein in sense orientation with respect to the maize 27 kD zein promoter that is located 5' to the cDNA fragment, and the 10 kD zein 3' end that is located 3' to the cDNA fragment, can be constructed. The cDNA fragment of this gene may be generated by polymerase chain reaction (PCR) of the cDNA clone using appropriate oligonucleotide primers. Cloning sites (NcoI or SmaI) can be incorporated into the oligonucleotides to provide proper orientation of the DNA fragment when inserted into the digested vector pML103 as described below. Amplification is then performed in a standard PCR. The amplified DNA is then digested with restriction enzymes NcoI and SmaI and fractionated on an agarose gel. The appropriate band can be isolated from the gel and combined with a 4.9 kb NcoI-SmaI fragment of the plasmid pML103. Plasmid pML103 has been deposited under the terms of the Budapest Treaty at ATCC (American Type Culture Collection, 10801 University Blvd., Manassas, Va. 20110–2209), and bears accession number ATCC 97366. The DNA segment from pML103 contains a 1.05 kb SalI-NcoI promoter fragment of the maize 27 kD zein gene and a 0.96 kb SmaI-SalI fragment from the 3' end of the maize 10 kD zein gene in the vector pGem9Zf (+) (Promega). Vector and insert DNA can be ligated at 15° C. overnight, essentially as described (Maniatis). The ligated DNA may then be used to transform *E. coli* XL1-Blue (Epicurian *Coli* XL-1 Blue™; Stratagene). Bacterial transformants can be screened by restriction enzyme digestion of plasmid DNA and limited nucleotide sequence analysis using the dideoxy chain termination method (Sequenase™ DNA Sequencing Kit; U.S. Biochemical). The resulting plasmid construct would comprise a chimeric gene encoding, in the 5' to 3' direction, the maize 27 kD zein promoter, a cDNA fragment encoding a hexose carrier protein, and the 10 kD zein 3' region.

The chimeric gene described above can then be introduced into corn cells by the following procedure. Immature corn embryos can be dissected from developing caryopses derived from crosses of the inbred corn lines H99 and LH132. The embryos are isolated 10 to 11 days after pollination when they are 1.0 to 1.5 mm long. The embryos are then placed with the axis-side facing down and in contact with agarose-solidified N6 medium (Chu et al., (1975) *Sci. Sin. Peking* 18:659–668). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every 2 to 3 weeks.

The plasmid, p35S/Ac (obtained from Dr. Peter Eckes, Hoechst Ag, Frankfurt, Germany) may be used in transformation experiments in order to provide for a selectable marker. This plasmid contains the Pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from Cauliflower Mosaic Virus (Odell et al. (1985) *Nature* 313:810–812) and the 3' region of the nopaline synthase gene from the T-DNA of the Ti plasmid of *Agrobacterium tumefaciens*.

The particle bombardment method (Klein et al., (1987) *Nature* 327:70–73) may be used to transfer genes to the callus culture cells. According to this method, gold particles (1 μm in diameter) are coated with DNA using the following technique. Ten μg of plasmid DNAs are added to 50 μL of a suspension of gold particles (60 mg per mL). Calcium chloride (50 μL of a 2.5 M solution) and spermidine free base (20 μL of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 μL of absolute ethanol, centrifuged again and the supernatant removed. The ethanol rinse is performed again and the particles resuspended in a final volume of 30 μL of ethanol. An aliquot (5 μL) of the DNA-coated gold particles can be placed in the center of a Kapton™ flying disc (Bio-Rad Labs). The particles are then accelerated into the corn tissue with a Biolistic™ PDS-1000/He (Bio-Rad Instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covered a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains gluphosinate (2 mg per liter) and lacks casein or proline. The tissue continues to grow slowly on this medium. After an additional 2 weeks the tissue can be transferred to fresh N6 medium containing gluphosinate. After 6 weeks, areas of about 1 cm in diameter of actively growing callus can be identified on some of the plates containing the glufosinate-supplemented medium. These calli may continue to grow when sub-cultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Fromm et al., (1990) *Bio/Technology* 8:833–839).

Example 5

Expression of Chimeric Genes in Dicot Cells

A seed-specific expression cassette composed of the promoter and transcription terminator from the gene encoding the β subunit of the seed storage protein phaseolin from the bean *Phaseolus vulgaris* (Doyle et al. (1986) *J. Biol. Chem.* 261:9228–9238) can be used for expression of the instant hexose carrier proteins in transformed soybean. The phaseolin cassette includes about 500 nucleotides upstream (5' ) from the translation initiation codon and about 1650 nucleotides downstream (3' ) from the translation stop codon of phaseolin. Between the 5' and 3' regions are the unique restriction endonuclease sites Nco I (which includes the ATG translation initiation codon), Sma I, Kpn I and Xba I. The entire cassette is flanked by Hind III sites.

The cDNA fragment of this gene may be generated by polymerase chain reaction (PCR) of the cDNA clone using appropriate oligonucleotide primers. Cloning sites can be incorporated into the oligonucleotides to provide proper orientation of the DNA fragment when inserted into the expression vector. Amplification is then performed as described above, and the isolated fragment is inserted into a pUC18 vector carrying the seed expression cassette.

Soybean embroys may then be transformed with the expression vector comprising a sequence encoding a hexose carrier protein. To induce somatic embryos, cotyledons, 3–5 mm in length dissected from surface sterilized, immature seeds of the soybean cultivar A2872, can be cultured in the light or dark at 26° C. on an appropriate agar medium for 6–10 weeks. Somatic embryos which produce secondary embryos are then excised and placed into a suitable liquid medium. After repeated selection for clusters of somatic embryos which multiplied as early, globular staged embryos, the suspensions are maintained as described below.

Soybean embryogenic suspension cultures can maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Kline et al. (1987) Nature (London) 327:70, U.S. Pat. No. 4,945,050). A DuPont Biolistic™ PDS 1000/HE instrument (helium retrofit) can be used for these transformations.

A selectable marker gene which can be used to facilitate soybean transformation is a chimeric gene composed of the 35S promoter from Cauliflower Mosaic Virus (Odell et al. (1985) Nature 313:810–812), the hygromycin phosphotransferase gene from plasmid pJR225 (from E. coli; Gritz et al. (1983) Gene 25:179–188) and the 3' region of the nopaline synthase gene from the T-DNA of the Ti plasmid of Agrobacterium tumefaciens. The seed expression cassette comprising the phaseolin 5' region, the fragment encoding the hexose carrier protein and the phaseolin 3' region can be isolated as a restriction fragment. This fragment can then be inserted into a unique restriction site of the vector carrying the marker gene.

To 50 $\mu$L of a 60 mg/mL 1 $\mu$m gold particle suspension is added (in order): 5 $\mu$L DNA (1 $\mu$g/$\mu$L), 20 $\mu$l spermidine (0.1 M), and 50 $\mu$L CaCl$_2$ (2.5 M). The particle preparation is then agitated for three minutes, spun in a microfuge for 10 seconds and the supernatant removed. The DNA-coated particles are then washed once in 400 $\mu$L 70% ethanol and resuspended in 40 $\mu$L of anhydrous ethanol. The DNA/particle suspension can be sonicated three times for one second each. Five $\mu$L of the DNA-coated gold particles are then loaded on each macro carrier disk.

Approximately 300–400 mg of a two-week-old suspension culture is placed in an empty 60×15 mm petri dish and the residual liquid removed from the tissue with a pipette. For each transformation experiment, approximately 5–10 plates of tissue are normally bombarded. Membrane rupture pressure is set at 1100 psi and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment with fresh media containing 50 mg/mL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 6

Expression of Chimeric Genes in Microbial Cells

The cDNAs encoding the instant hexose carrier proteins can be inserted into the T7 E. coli expression vector pBT430. This vector is a derivative of pET-3a (Rosenberg et al. (1987) Gene 56:125–135) which employs the bacteriophage T7 RNA polymerase/T7 promoter system. Plasmid pBT430 was constructed by first destroying the EcoR I and Hind III sites in pET-3a at their original positions. An oligonucleotide adaptor containing EcoR I and Hind III sites was inserted at the BamH I site of pET-3a. This created pET-3aM with additional unique cloning sites for insertion of genes into the expression vector. Then, the Nde I site at the position of translation initiation was converted to an Nco I site using oligonucleotide-directed mutagenesis. The DNA sequence of pET-3aM in this region, 5'-CATATGG, was converted to 5'-CCCATGG in pBT430.

Plasmid DNA containing a cDNA may be appropriately digested to release a nucleic acid fragment encoding the protein. This fragment may then be purified on a 1% NuSieve GTG™ low melting agarose gel (FMC). Buffer and agarose contain 10 $\mu$g/ml ethidium bromide for visualization of the DNA fragment. The fragment can then be purified from the agarose gel by digestion with GELase™ (Epicentre Technologies) according to the manufacturer's instructions, ethanol precipitated, dried and resuspended in 20 $\mu$L of water. Appropriate oligonucleotide adapters may be ligated to the fragment using T4 DNA ligase (New England Biolabs, Beverly, Mass.). The fragment containing the ligated adapters can be purified from the excess adapters using low melting agarose as described above. The vector pBT430 is digested, dephosphorylated with alkaline phosphatase (NEB) and deproteinized with phenol/chloroform as decribed above. The prepared vector pBT430 and fragment can then be ligated at 16° C. for 15 hours followed by transformation into DH5 electrocompetent cells (GIBCO BRL). Transformants can be selected on agar plates containing LB media and 100 $\mu$g/mL ampicillin. Transformants containing the gene encoding the hexose carrier protein are then screened for the correct orientation with respect to the T7 promoter by restriction enzyme analysis.

For high level expression, a plasmid clone with the cDNA insert in the correct orientation relative to the T7 promoter can be transformed into E. coli strain BL21(DE3) (Studier et al. (1986) J. Mol. Biol. 189:113–130). Cultures are grown in LB medium containing ampicillin (100 mg/L) at 25° C. At an optical density at 600 nm of approximately 1, IPTG (isopropylthio-β-galactoside, the inducer) can be added to a final concentration of 0.4 mM and incubation can be continued for 3 h at 25°. Cells are then harvested by centrifugation and re-suspended in 50 $\mu$L of 50 mM Tris-HCl at pH 8.0 containing 0.1 mM DTT and 0.2 mM phenyl methylsulfonyl fluoride. A small amount of 1 mm glass beads can be added and the mixture sonicated 3 times for about 5 seconds each time with a microprobe sonicator. The mixture is centrifuged and the protein concentration of the supernatant determined. One $\mu$g of protein from the soluble fraction of the culture can be separated by SDS-polyacrylamide gel electrophoresis. Gels can be observed for protein bands migrating at the expected molecular weight.

What is claimed is:

1. An isolated polynucleotide comprising:
   (a) a nucleotide sequence encoding a polypeptide having hexose carrier activity, wherein the amino acid sequence of the polypeptide and the amino acid sequence of SEQ ID NO:16 have at least 95% identity based on the Clustal alignment method, or
   (b) the complement of the nucleotide sequence, wherein the complement and the nucleotide sequence contain the same number of nucleotides and are 100% complementary.

2. The polynucleotide of claim 1, wherein the nucleotide sequence comprises the nucleotide sequence of SEQ ID NO:15.

3. The polynucleotide of claim 1, wherein the amino acid sequence of the polypeptide comprises the amino acid sequence of SEQ ID NO:16.

4. A vector comprising the polynucleotide of claim 1.

5. A recombinant DNA construct comprising the polynucleotide of claim 1 operably linked to at least one regulatory sequence.

6. A method for transforming a cell comprising transforming a cell with the polynucleotide of claim 1.

7. A cell comprising the recombinant DNA construct of claim 5.

8. A method for producing a plant comprising transforming a plant cell with the polynucleotide of claim 1 and regenerating a plant from the transformed plant cell.

9. A plant comprising the recombinant DNA construct of claim 5.

10. A seed comprising the recombinant DNA construct of claim 5.

* * * * *